United States Patent [19]

Chen et al.

[11] Patent Number: 5,254,580
[45] Date of Patent: Oct. 19, 1993

[54] 7,8-CYCLOPROPATAXANES

[75] Inventors: Shu-Hui Chen, Hamden; Vittorio Farina, West Hartford, both of Conn.

[73] Assignee: Bristol-Myers Squibb Company, New York, N.Y.

[21] Appl. No.: 29,819

[22] Filed: Mar. 11, 1993

Related U.S. Application Data

[63] Continuation-in-part of Ser. No. 6,423, Jan. 19, 1993, which is a continuation of Ser. No. 907,261, Jul. 1, 1993, abandoned.

[51] Int. Cl.$^5$ .................... A01N 43/02; C07C 305/00
[52] U.S. Cl. ................................. 514/449; 549/510; 549/511
[58] Field of Search ................ 549/510, 511; 514/449

[56] References Cited

U.S. PATENT DOCUMENTS

| | | | |
|---|---|---|---|
| 4,814,470 | 3/1989 | Colin et al. | 514/449 |
| 4,876,399 | 10/1989 | Holton et al. | 514/449 |
| 4,960,790 | 10/1990 | Stella et al. | 514/449 |
| 5,015,744 | 5/1991 | Holton et al. | 549/520 |
| 5,136,060 | 8/1992 | Holton et al. | 549/510 |

FOREIGN PATENT DOCUMENTS

| | | | |
|---|---|---|---|
| 400971A2 | 12/1990 | European Pat. Off. | 514/449 |
| 534707A1 | 3/1993 | European Pat. Off. | 514/449 |
| 534708A1 | 3/1993 | European Pat. Off. | 514/449 |
| 534709A1 | 3/1993 | European Pat. Off. | 514/449 |

OTHER PUBLICATIONS

S. Cai et al, "Application of Protease-Catalyzed Regioselective Esterification in Synthesis of 6'-Deoxy-6'-fluoro-and 6-Deoxy-6-fluorolactosides", J. Org. Chem., 57, No. 12, pp. 3431–3437, 1992.

G. I. Georg, et al, "Synthesis of Biologically Active Taxol Analogues with Modified Phenylisoserine Side Chains", Journal of Medicinal Chemistry, 35, pp. 4230–4237, 1992.

G. I. Georg, et al, "Semisynthesis and Biological Activity of Taxol Analogues: Baccatin III 13-(N-benzoyl-(2'R,3'S)-3'-(p-tolyl)isoserinate), Baccatin III 13-(N-(p-toluoyl)-(2'R,3'S)-3'-phenylisoserinte), Baccatin III 13-(N-benzoyl-(2'R,3'S)-3'-(p-trifluoromethylphenyl)isoserinate), Baccatin III 13-(N-(p-trifluoromethylbenzoyl)-(2'R,3'S)-3'-phenylisoserinate)", Bioorganic & Medical Chemistry Letters, 2, No. 12, pp. 1751–1754, 1992.

(List continued on next page.)

*Primary Examiner*—James H. Reamer
*Attorney, Agent, or Firm*—William T. Han

[57] ABSTRACT

An antitumor compound of formula I in which $R^1$ is —$COR^z$ in which $R^z$ is t-butyloxy, $C_{1-6}$ alkyl, $C_{2-6}$ alkenyl, $C_{2-6}$ alkynyl, $C_{3-6}$ cycloalkyl, or phenyl, optionally substituted with one to three same or different $C_{1-6}$ alkyl, $C_{1-6}$ alkoxy, halogen or —$CF_3$ groups;

$R^2$ is $C_{1-6}$ alkyl, $C_{2-6}$ alkenyl, $C_{2-6}$ alkynyl, $C_{3-6}$ cycloalkyl, or a radical of the formula —W—$R^x$ in which W is a bond, $C_{2-6}$ alkenediyl, or —$(CH_2)_t$—, in which t is one to six; and $R^x$ is naphthyl, furyl, thienyl or phenyl, and furthermore $R^x$ can be optionally substituted with one to three same or different $C_{1-6}$ alkyl, $C_{1-6}$ alkoxy, halogen or —$CF_3$ groups;

$R^3$ is OCOR, —OCOOR, H, or OH; $R^4$ is hydrogen; or $R^3$ and $R^4$ jointly form a carbonyl group; and R is $C_{1-6}$ alkyl.

Also provided by this invention are pharmaceutical formulations (compositions) and a method of treating mammalian tumors with a compound of formula I.

11 Claims, No Drawings

OTHER PUBLICATIONS

G. I. Georg, et al, "Novel Biologically Active Taxol Analogues: Baccatin III 13-(N-(p-Chlorobenzoyl)-2'R,3'S)-3'-phenylisoserinate) and Baccatin III 13-(-N-Benzoyl-(2'R,3'S)-3'-(p-chlorophenyl)isoserinate)", Bioorganic & Medical Chemistry Letters, 2, No. 4, pp. 295-298, 1992.

F. Gueritte-Voegelein et al, "Relationships between the Structure of Taxol Analogues and Their Antimitotic Activity," Journal of Medicinal Chemistry, 1991, 34, pp. 992-998.

D. G. I. Kingston, et al, "The Chemistry of Taxol, A Clinically Useful Anticancer Agent", Journal of Natural Products, 53, No. 1, pp. 1-12, 1990.

T. Kobayashi, et al, "Synthesis of 7-Fluoro-B-homo-1-9-norcholest-5(10)-en-3$\beta$-ol Acetate", Chem. Pharm. Bull., 30, pp. 3082-3087, 1982.

A. M. MacLeod, et al, "Facile Synthesis of the 4-Azatricyclo[2.2.1.0$^{2,6}$]heptane System," J. Chem. Soc. Chem. Commun., pp. 100-102, 1990.

N. F. Magri and D. G. I. Kingston, "Modified Taxols, 2.[1] Oxidation Products of Taxol", J. Org. Chem., 51, pp. 797-802, 1986.

N. F. Magri and D. G. I. Kingston, "Modified Taxols, 4. Synthesis and Biological Activity of Taxols Modified in the Side Chain", Journal of Natural Products, 51, No. 2, pp. 298-306, 1988.

W. P. McGuire, M.D. et al, "Taxol: A Unique Antineoplastic Agent with Significant Activity in Advanced Ovarian Epithelial Neoplasms," Annals of Internal Medicine, Aug. 15, 1989, 111, No. 4, pp. 273-279., E. Napolitano, et al, "Synthesis of 1,11$\beta$-Ethanoestra-1,3,5(10)-triene-3,17$\beta$-diol: a Novel Bridged Steriod Derivative", J. Chem. Soc. Chem. Commun., pp. 1330-1331, 1989.

I. Ojima, et al, "Efficient and Practical Asymmetric Synthesis of the Taxol C-13 Side Chain, N-Benzoyl-(2R,3S)-3-phenylisoserine, and Its Analogues via Chiral 3-Hydroxy-4-aryl-$\beta$-lactams through Chiral Ester Enolate-Imine Cyclocondensation", J. Org. Chem., 56, pp. 1681-1683, 1991.

I. Ojima, et al, "New and Efficient Approaches to the Semisynthesis of Taxol and its C-13 Side Chain Analogs by means of B-Lactam Synthon Method", Tetrahedron, 48, No. 34, pp. 6985-7012, 1992.

K. W. Pankiewicz, et al, "A Synthesis of 9-(2-Deoxy-2-fluoro-$\beta$-D-arabiofuranosyl)adenine and Hypoxanthine. An effect of C3'-Endo to C2'-Endo Conformational Shift on the Reaction Course of 2'-Hydroxyl Group with DAST[1]", J. Org. Chem., 57, No. 2, pp. 553-559, 1992.

I. P. Street and S. G. Withers, "Fluorination of Protected Mannose Derivatives using Diethylaminosulfur Trifluoride", Can. J. Chem., 64, pp. 1400-1403, 1986.

C. S. Swindell et al, "Biologically Active Taxol Analogues with Deleted A-Ring Side Chain Substituents and Variable C-2' Configurations," Journal of Medicinal Chemistry, 1991, 34, pp. 1176-1184.

S. Takano, et al, "Regioselective Formation of 3-tertAlkoxy-1,2-Glycols from 2,3-O-Alkylidenetriols with Trimethylaluminum", Tetrahedron Letters, 29, No. 15, pp. 1823-1824, 1988.

7,8-CYCLOPROPATAXANES

CROSS REFERENCE TO RELATED APPLICATIONS

This application is a continuation-in-part application of Ser. No. 08/006,423, filed Jan. 19, 1993, which is herein incorporated by reference in its entirety and which in turn is a continuation application of Ser. No. 07/907,261, filed Jul. 1, 1992 abandoned.

FIELD OF INVENTION

The present invention provides compounds having antitumor activities.

BACKGROUND OF INVENTION

Taxol was first isolated from the stem bark of Western Yew, Taxus brevifolia Nut. (Taxaceae) and has the following structure (with the (C)2'-, 7-, 8-, 10- and 13th-positions indicated):

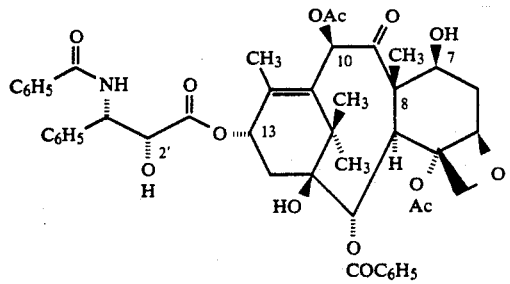

In ongoing clinical trials sponsored by the National Cancer Institute (NCI), taxol has shown promising results in fighting advanced cases of ovarian, breast, and other cancers.

Taxol is unique among antimitotic drugs in that it promotes the assembly of stable microtubules from tubulin even under otherwise unfavorable conditions. The drug binds to microtubules, stabilizing them from depolymerization, thus disrupting the tubulin-microtubule equilibrium and consequently inhibiting mitosis. The mechanism of action, toxicology, clinical efficacy, etc. of taxol are reviewed in a number of articles, such as in the article by Rowinsky et al. in *Taxol: A Novel Investigational Antimicrotubule Agent*, *J. Natl. Cancer Inst.*, 82: pp 1247-1259 (1990).

Since the discovery of its significant effectiveness in cancer treatment, many laboratories have launched programs to design taxol analogues in search of better pharmacological profiles. Out of such programs, for example, was the discovery of taxotere of the formula

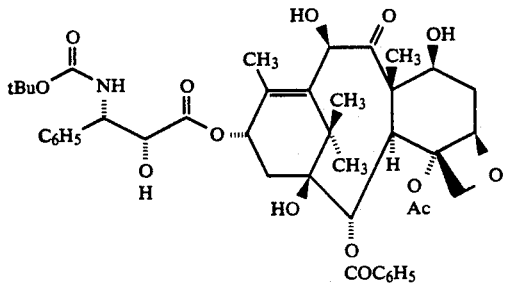

See, Biologically Active Taxol Analogues with Deleted A-Ring Side Chain Substitutents and Variable C-2' Configurations, *J. Med. Chem.*, 34, pp 1176-1184 (1991); Relationships between the Structure of Taxol Analogues and Their Antimitotic Activity, *J. Med. Chem.*, 34, pp 992-998 (1991).

The present invention relates to structurally novel taxol derivatives with antitumor activities.

SUMMARY OF INVENTION

The present invention provides taxol derivatives of formula I

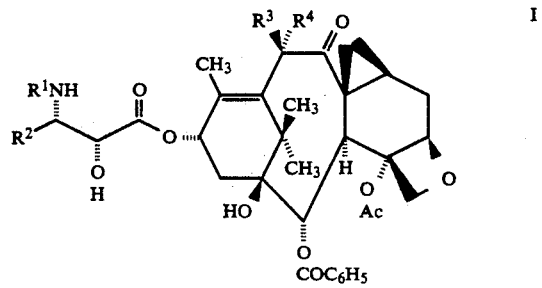

in which $R^1$ is —$COR^z$ in Which $R^z$ is t-butyloxy, $C_{1-6}$ alkyl, $C_{2-6}$ alkenyl, $C_{2-6}$ alkynyl, $C_{3-6}$ cycloalkyl, or phenyl, optionally substituted with one to three same or different $C_{1-6}$ alkyl, $C_{1-6}$ alkoxy, halogen or —$CF_3$ groups;

$R^2$ is $C_{1-6}$ alkyl, $C_{2-6}$ alkenyl, $C_{2-6}$ alkynyl, $C_{3-6}$ cycloalkyl, or a radical of the formula —W—$R^x$ in which W is a bond, $C_{2-6}$ alkenediyl, or —$(CH_2)_t$—, in which t is one to six; and $R^x$ is naphthyl, furyl, thienyl or phenyl, and furthermore $R^x$ can be optionally substituted with one to three same or different $C_{1-6}$ alkyl, $C_{1-6}$ alkoxy, halogen or —$CF_3$ groups;

$R^3$ is OCOR, —OCOOR, H, or OH; $R^4$ is hydrogen; or $R^3$ and $R^4$ jointly form a carbonyl group; and R is $C_{1-6}$ alkyl.

Also provided by this invention are pharmaceutical formulations (compositions) and a method of treating mammalian tumors with a compound of formula I.

DETAILED DESCRIPTION OF INVENTION

The present invention provides taxol derivatives of formula I

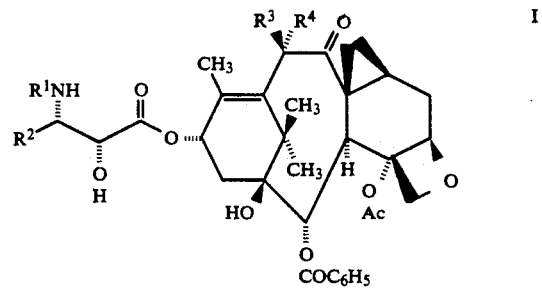

in which $R^1$ is —$COR^z$ in which $R^z$ is t-butyloxy, $C_{1-6}$ alkyl, $C_{2-6}$ alkenyl, $C_{2-6}$ alkynyl, $C_{3-6}$ cycloalkyl, or phenyl, optionally substituted with one to three same or different $C_{1-6}$ alkyl, $C_{1-6}$ alkoxy, halogen or —$CF_3$ groups;

$R^2$ is $C_{1-6}$ alkyl, $C_{2-6}$ alkenyl, $C_{2-6}$ alkynyl, $C_{3-6}$ cycloalkyl, or a radical of the formula —W—$R^x$ in which W is a bond, $C_{2-6}$ alkenediyl, or —$(CH_2)_t$—, in which t is one to six; and $R^x$ is naphthyl, furyl, thienyl or phenyl, and furthermore $R^x$ can be optionally substituted with one to three same or different $C_{1-6}$ alkyl, $C_{1-6}$ alkoxy, halogen or —$CF_3$ groups;

$R^3$ is OCOR, —OCOOR, H, or OH; $R^4$ is hydrogen; or $R^3$ and $R^4$ jointly form a carbonyl group; and R is $C_{1-6}$ alkyl.

In the instant application, the numbers in subscript after the symbol "C" define the number of carbon atoms a particular group can contain. For example, $C_{1-6}$ alkyl refers to straight and branched chain alkyl groups with one to six carbon atoms and such groups include methyl, ethyl, n-propyl, isopropyl, n-butyl, t-butyl, n-pentyl, n-hexyl, 3-methylpentyl, or the like alkyl groups; $C_{2-6}$ alkenyl refers to straight or branched alkenyl groups such as vinyl, allyl, 1-propenyl, isopropenyl, 1-butenyl, 2-butenyl, 3-butenyl, methallyl, 1,1-dimethylallyl, 1-hexenyl, 2-hexenyl, or the like groups; $C_{3-6}$ cycloalkyl refers to cyclopropyl, cyclobutyl, cyclopentyl, or cyclohexyl; $C_{2-6}$ alkynyl refers to straight or branched alkynyl groups such as ethynyl, propargyl (2-propynyl), 1-propynyl, 2-butynyl, 3-butynyl, 1-hexynyl, 4-methyl-2-pentynyl, and the like groups; $C_{2-6}$ alkenediyl refers to groups such as ethylene-1,2-diyl (vinylene), 2-methyl-2-butene-1,4-diyl, 2-hexene-1,6-diyl, and the like groups; $C_{1-6}$ alkyloxy (alkoxy) refers to straight or branched alkyloxy group such as methoxy, ethoxy, n-propoxy, i-propoxy, n-butoxy, t-butoxy (t-butyloxy), n-pentyloxy, n-hexyloxy, or 3-methylpentyloxy, to name a few; and halogen refers to fluorine, chlorine, bromine, or iodine. In the instant application all symbols once defined retain the same meaning until they are redefined.

The synthesis of a compound of formula I can be accomplished by a wide variety of methods. The synthetic descriptions and specific examples that follow are only intended for the purpose of illustration, and are not to be construed as limiting in any manner ways to make compounds of the present invention by other methods.

In one embodiment, a compound of formula I may be made by a process of Scheme I. In the Scheme, a compound of formula II is reacted with DAST to afford a compound of formula III. As used herein, $R^5$ is hydrogen, acetyloxy or —$OR^8$; $R^6$ is hydrogen; or $R^5$ and $R^6$ jointly form a carbonyl group; $R^7$ and $R^8$ each is same or different conventional hydroxy protecting group. Removal of hydroxy protecting group(s) from a compound of formula III affords a compound of formula I.

A compound of formula II can be made by a wide array of conventional methods using conventional starting materials. For example, in one embodiment, a compound of formula IV, in which $R^9$ is acetyloxy or hydrogen, may be treated with a base such as DBU to afford a compound of formula V. Further protection of 2'-hydroxy group affords a compound of formula II$^1$, a compound within the scope of formula II. Scheme II. In another embodiment, a compound of formula II$^2$ can be made by a process of Scheme III. In the Scheme, a compound of formula IV$^1$ can be treated with $ZnBr_2$ which simultaneously epimerizes 7-hydroxy and deacetylates 10-acetyloxy to afford a compound of formula VI. The unmasked 10-hydroxy and 2'-hydroxy can be protected with the same or different conventional hydroxy protecting groups in Step (b) to afford additional compounds within formula II. (Often it is advantageous to select different hydroxy protecting groups for $R^7$ and $R^8$ which would to allow one protecting group to be removed without affecting the other. In general the reactivity toward a hydroxy protecting agent is greater for the 2'-hydroxy group than that of the 10-hydroxy group.) As a further example, a compound of formula VI may be treated with $MnO_2$ to afford a compound of formula X. Scheme IV. Upon protecting 2'-hydroxy, a compound of formula II$^3$ can be obtained.

SCHEME I

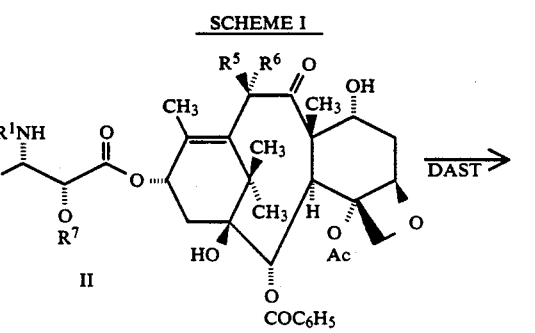

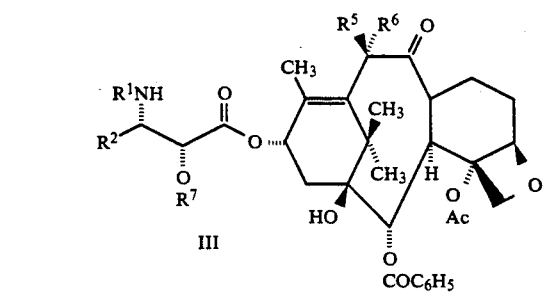

SCHEME II

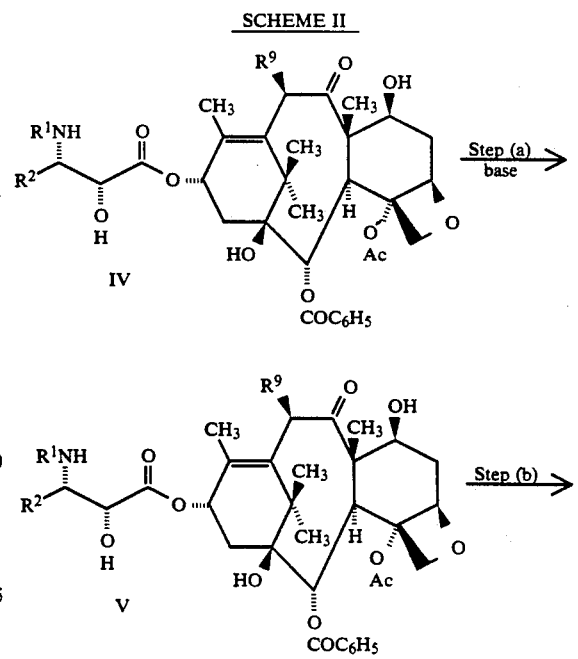

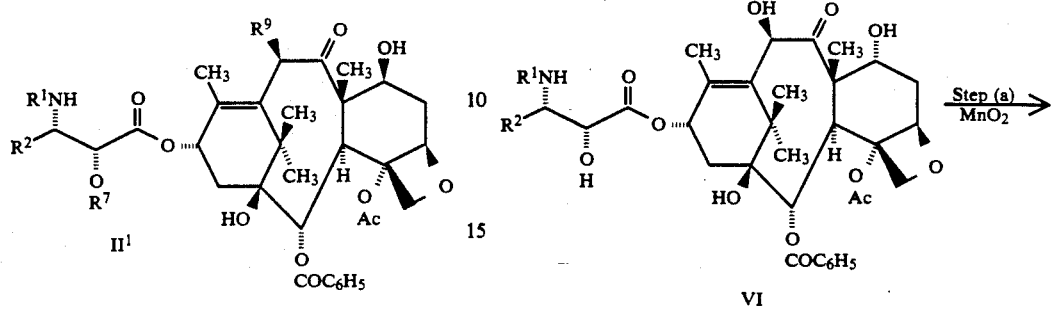
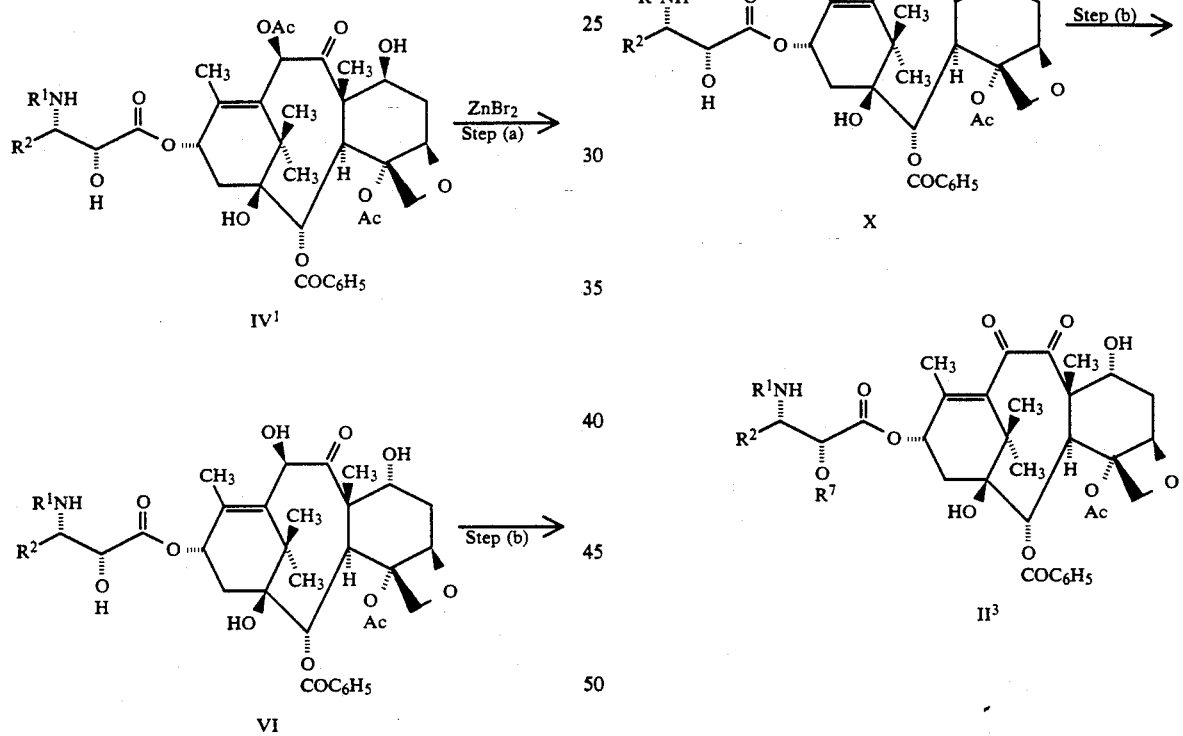
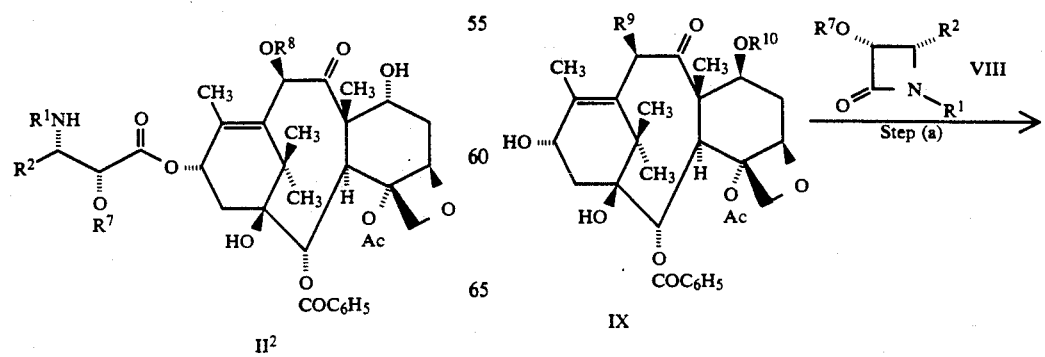

-continued
Scheme V

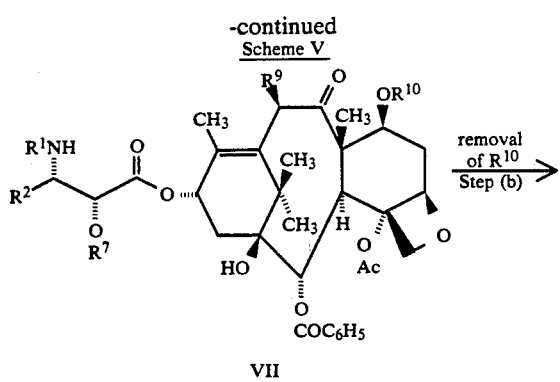

VII

IV

A compound of formula IV can be obtained by a wide array of methods. As an illustration, an azetidinone of formula VIII may be reacted with a compound of formula IX (a baccatin III derivative) to afford a compound of formula VII, in which $R^{10}$ is also a conventional hydroxy protecting group, but which is preferably a different hydroxy protecting group from $R^7$ of formula VIII. A compound of formula IX in which $R^{10}$ is triethylsilyl is reported in U.S. Pat. No. 4,924,011, issued to Denis et al. on May 8, 1990. Syntheses of other 7-hydroxy protected baccatin III compounds of formula IX in which $R^{10}$ is other than trialkylsilyl shall be obvious to any person skilled in the art. The general class of azetidinones of formula VIII are known. Their syntheses or syntheses of their precursors have been reported such as by Holton in European Patent Application 0,400,971 A2 published on Dec. 5, 1990; by Ojima et al. in Tetrahedron, 48, No. 34, pp 6985-7012 (1992); Journal of Organic Chemistry, 56, pp 1681-1683 (1991); and Tetrahedron Letters, 33, No. 39, pp 5737-5740 (1992); and by Palomo et al. in Tetrahedron Letters, 31, No. 44, pp 6429-6432 (1990); all five disclosures are herein incorporated by reference in their entirety. The methods that can be adapted to variations in order to produce other azetidinones within the scope of formula VIII, but not specifically disclosed in the above five references or reported elsewhere, will be obvious to anyone skilled in the art. Furthermore, European Patent Application 0,400,971 A2 and Tetrahedron, 48, No. 34, pp 6985-7012 (1992) also describe processes whereby the class of azetidinones of formula VIII are reacted with (C)13-hydroxy group of baccatin III derivatives or sodium alkoxide thereof to afford taxol analogues with a variety of (C)13-side chains. In Step (a) of Scheme V, it is advantageous to convert the hydroxy group on the (C)13-carbon into a metal alkoxide before the coupling. The metal cation of said metal alkoxide is preferably selected from Group Ia or IIa metals. The formation of a desired metal alkoxide may be done by reacting a compound of formula IX with a strong metal base, such as lithium diisopropylamide, $C_{1-6}$ alkyllithium, lithium bis(trimethylsilyl)amide, phenyllithium, sodium hydride, potassium hydride, lithium hydride, or the like base. For example when lithium alkoxide is desired, a compound of formula IX may be reacted with n-butyllithium in an inert solvent such as tetrahydrofuran. Removal of hydroxy protecting groups from a compound of formula VII in Step (b), affords a compound of formula IV.

As used herein, conventional hydroxy protecting groups are moieties which can be employed to block or protect the hydroxy function and they are well known to those skilled in the art. Preferably, said groups are those which can be removed by methods which result in no appreciable destruction to the remaining portion of the molecule. Examples of such readily removable hydroxy protecting groups include chloroacetyl, methoxymethyl, 2,2,2-trichloroethoxymethyl, 2,2,2-trichloroethyloxycarbonyl, tetrahydropyranyl, tetrahydrofuranyl, t-butyl, benzyl, p-nitrobenzyl, p-methoxybenzyl, diphenylmethyl, tri$C_{1-6}$alkylsilyl, triphenylsilyl, 1-ethoxyethyl, allyloxycarbonyl, and the like. Preferred protecting groups for hydroxy groups of taxol and a derivative thereof are 1-ethoxyethyl, triethylsilyl, allyloxycarbonyl, 2,2,2-trichloroethylcarbonyl and benzyloxycarbonyl. Other suitable protecting groups which can be used are found in Chapter 2 of "Protecting Groups in Organic Synthesis", Second Ed., by Theodora W. Greene and Peter G. M. Wuts (1991, John Wiley & Sons); the disclosure thereof is herein incorporated by reference.

As in Scheme VI, when a hydroxy protecting group $R^8$ is selectively removed from a compound of formula III[1] and acylated with RCOOH or ROOCG, in which G is a leaving group such as halogen or 1-imidazoyl, on (C)10-hydroxy, a compound of formula XIII can be obtained. Removal of $R^7$ from a compound of formula XIII, in Which $R^{12}$ is RCOO- or ROOCO-, affords additional compounds within the scope of formula I.

As used herein, "acylation" also means the derivatization of a hydroxy group into a carbonate group.

The art of acylating a hydroxy group with a carboxylic acid is well known in the art. Particularly useful to the present invention are those that employ dehydrating agents such as dicyclohexylcarbodiimide (DCC), alkyl chloroformate and triethylamine, pyridinium salts-$Bu^3N$, phenyl dichlorophosphate, DCC and an aminopyridine, 2-chloro-1,3,5-trinitrobenzene and pyridine, polyphosphate ester, chlorosulfonyl isocyanate, chlorosilanes, $MeSO_2Cl$-triethylamine, $Ph_3P$-$CCl_4$-triethylamine, or N,N'-carbonyldiimidazole, to name a few. References to these reagents can be found in "Advanced Organic Chemistry", 3rd Ed., by Jerry March, pp 348-351 (1985, John Wiley & Sons). More particularly advantageous dehydrating system is comprised of DCC and 4-dimethylaminopyridine (4-DMAP).

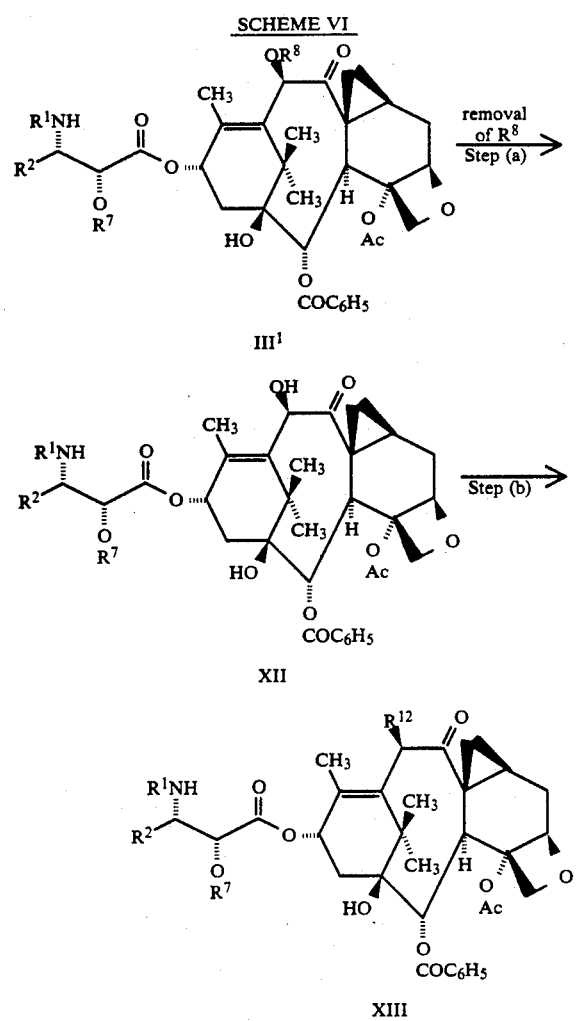

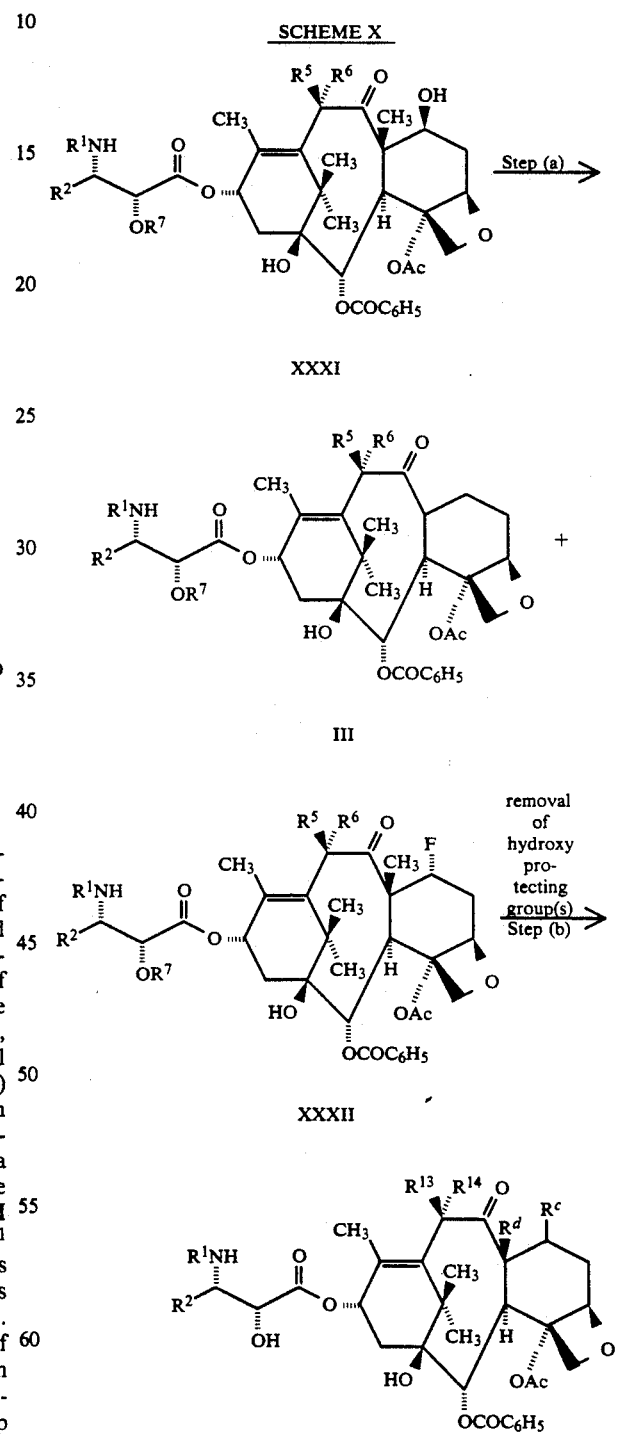

moved. The process of Scheme XI may be carried out in the presence of 7-alpha-fluorotaxane XXXIII which does not materially affect each steps: 7-alpha-fluorotaxane of formula XXXVIII may be separated from 7,8-cyclopropataxane at the end.

It has also been discovered that when a taxol derivative with the 7-hydroxy group in its natural beta position, as for example represented by a compound of formula XXXI, is treated with DAST in halogenated solvent, such as methylene chloride, a 7,8-cyclopropataxane of formula III and a 7-alphafluorotaxane of formula XXXII are simultaneously obtained. (If the reaction of Step(a) is conducted in ethereal solvent, such as tetrahydrofuran or tetrahydrofuran/diethyl ether, 7-alpha-fluorotaxane is usually the sole product.) The compound of formula III may be separated from the compound of formula XXXII, and hydroxy protecting group(s) removed to afford a compound of formula $I^1$; or, if desired, hydroxy protecting group(s) may be removed from a mixture of compounds of formula III and XXXII, and the desired compound of formula $I^1$ separated from the resultant mixture. Scheme XI. As used herein, $R^{13}$ is hydrogen, acetyloxy or —OH; $R^{14}$ is hydrogen; or $R^{13}$ and $R^{14}$ jointly form a carbonyl group.

In Scheme XI, the (C)13-side chain of compound of formula $I^1$ may be removed with a reducing agent such as tetrabutylammonium borohydride to afford a baccatin III derivative of formula XXXV. Analogous to Step (a) of Scheme V, a compound of formula XXXV is subsequently reacted with a beta-lactam of formula VIII, in which $R^1$ and $R^2$ may be different from those in formula $I^1$, to afford a compound of formula XXXVII, from which $R^7$ hydroxy protecting group may be re- XXXIII:
$R^c$ = α-fluoro, $R^d$ = $CH_3$
$I^1$: $R^c$ and $R^d$ together form β-cyclopra

SCHEME XI

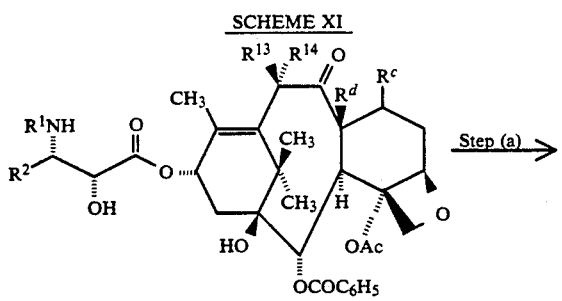

XXXIII: $R^c = \alpha$-fluoro, $R^d = CH_3$
$I^1$: $R^c$ and $R^d$ together form $\beta$-cyclopra

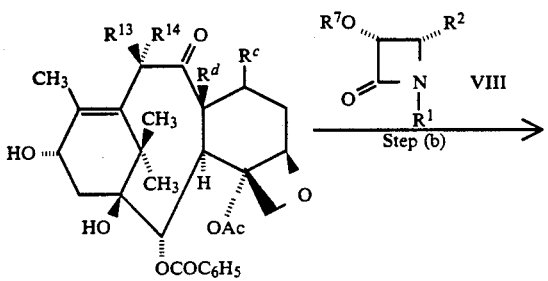

XXXIV: $R^c = \alpha$-fluoro, $R^d = CH_3$
XXXV: $R^c$ and $R^d$ together form $\beta$-cyclopra

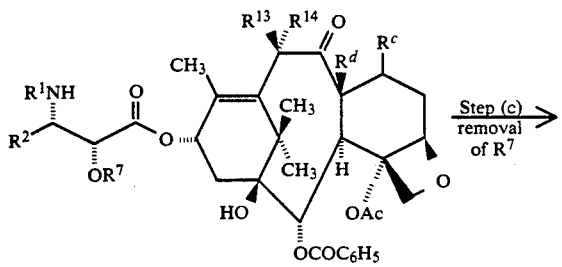

XXXVI: $R^c = \alpha$-fluoro, $R^d = CH_3$
XXXVII: $R^c$ and $R^d$ together form $\beta$-cyclopra

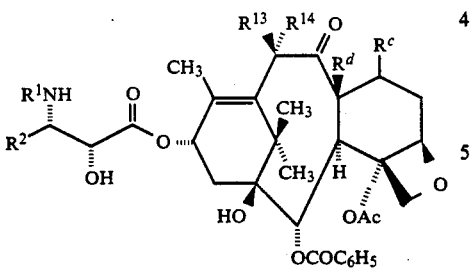

XXXVIII: $R^c = \alpha$-fluoro, $R^d = CH_3$
$I^2$: $R^c$ and $R^d$ together form $\beta$-cyclopra

DESCRIPTION OF SPECIFIC EMBODIMENTS

The structural formulae as drawn in the instant application are believed to best represent the structures of compounds of the present invention. However, some compounds within the scope of the invention may exist as other tautomeric forms, in which hydrogen atoms are transposed to other parts of the molecules and the chemical bonds between the atoms of the molecules are consequently rearranged. It should be understood that the structural formulae represent all tautomeric forms, insofar as they may exist.

The specific examples which follow illustrate the synthesis of representative compounds of the instant invention and are not to be construed as limiting the invention in sphere or scope. The methods may be adapted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiplet (m), doublet (d), quartet (q), triplet (t), doublet of doublet (dd), doublet of triplet (dt), and doublet of quartet (dq). The solvents employed for taking NMR spectra are DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave number ($cm^{-1}$) having functional group identification value.

Celite is a registered trademark of the Johns-Manville Products Corporation for diatomaceuous earth.

The abbreviations used herein are conventional abbreviations widely employed in the art. Some of which are:

| | |
|---|---|
| Ac | acetyl |
| Ar | aryl |
| Bn | Benzyl |
| Bz | benzoyl |
| Cbz | benzyloxycarbonyl |
| DAST | diethylaminosulfur trifluoride |
| DBU | 1,8-diazabicyclo[5.4.0]undec-7-ene |
| DCI | desorption chemical ionization |
| FAB | fast atom bombardment |
| h | hour(s) |
| HRMS | high resolution mass spectrometry |
| min | minute(s) |
| MS | mass spectrometry |
| NOBA | m-nitrobenzylalcohol |
| Ph | phenyl |
| tBu | tertiarybutyl |
| TES | triethylsilyl |
| TROC (Troc) | 2,2,2-trichloroethyloxycarbonyl (trichloroethyloxycarbonyl) |
| v/v | volume/volume |
| Y | yield |

EXAMPLE 1

2'-O-Benzyloxycarbonyl-7-epi-hydroxytaxol (IIa)

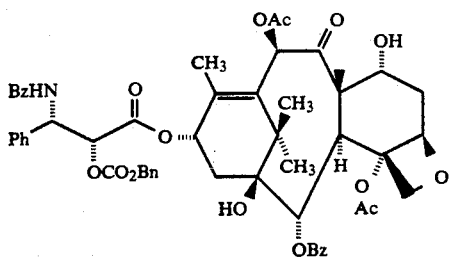

7-Epi-hydroxytaxol (237 mg, 0.278 mmol), which is available as described by Huang et al. in J. Nat. Prod., 1986, 49, pp 665–9, was dissolved in dry dichloromethane (5.6 mL). To this solution at 0° C. was added i-Pr$_2$Net (0.145 mL, 0.834 mmol), followed by BnOCOCl (0.119 mL, 0.834 mmol). The reaction was stirred at that temperature for 3 h. Then the solvent was removed in vacuo, and the residue was chromatographed (eluted with 50% ethyl acetate in hexanes) to afford 257 mg (Y: 81%) of the desired product IIa as a foam; $^1$H-NMR (CDCl$_3$) δ 8.12–7.19 (m, 20H, 6.88 (d, J=9.5 Hz, 1H), 6.76 (s, 1H, 6.20 (m, 1H), 5.94 (dd, J=2.7 Hz, J'=9.3 Hz, 1H), 5.69 (d, J=7.5 Hz, 1H), 5.40 (d, J=2.8 Hz, 1H), 5.09 (AB q, 2H), 4.86 (dd, J=3.6 Hz, J'=12.3 Hz, 1H), 4.65 (s, 2H), 4.52 (s, 2H), 3.86 (d, J=7.5 Hz, 1H), 3.65 (s, 1H), 2.48–1.01 (m, 22H, including singlets at 2.48, 2.12, 1.83, 1.60, 1.14, 1.06, 3H each); HRMS calcd for C$_{55}$H$_{58}$NO$_{16}$(MH): 988.3756, found: 988.3732.

EXAMPLE 2

2'-O-Benzyloxycarbonyl-7-deoxy-8-desmethyl-7,8-cyclopropataxol (IIIa) and compound XIa

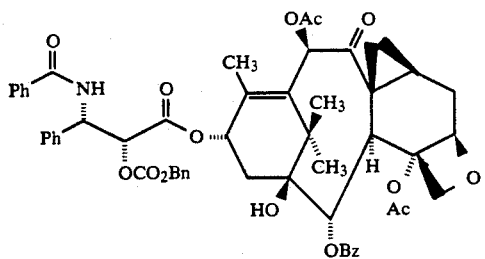

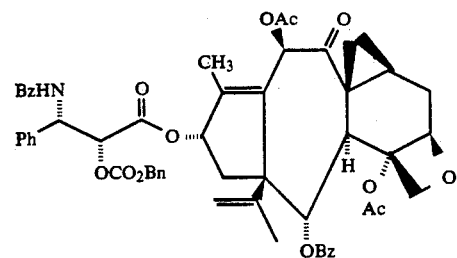

Compound IIa (162.3 mg, 0.164 mmol) was dissolved in dry dichloromethane (3.3 mL) at 0° C. To this solution was added DAST (43.5 μL, 0.328 mmol). After 2 h at that temperature, another batch of DAST (43.5 μL, 0.328 mmol) was added. The reaction mixture was stirred at 0° C. for 1 h and then at room temperature overnight. After 16 h, the reaction was quenched with a few drops of water, and the solvent was removed in vacuo. The residue was purified by silica gel chromatography (eluted with 40% ethyl acetate in hexanes) to afford 99.6 mg (Y: 63%) of compounds IIIa and XIa as a mixture together with 44.6 mg (Y: 27.5%) of starting material IIa. The ratio of compound IIIa to XIa was determined to be ca. 1:1 by HPLC analysis. Preparative HPLC (silica gel, eluted with 40% ethyl acetate/hexane) afforded compound IIIa as a foam.

Compound IIIa: $^1$H-NMR (CDCl$_3$) δ 8.14–8.11 (m, 2H), 7.65–7.12 (m, 18H), 6.86 (d, J=9.6 Hz, 1H), 6.34 (s, 1H), 6.24 (m, 1H), 5.95 (dd, J=2.6 Hz, J'=9.4 Hz, 1H), 5.61 (d, J=7.7 Hz, 1H), 5.39 (d, J=2.7 Hz, 1H), 5.10 (AB q, 2H), 4.69 (m, 1H), 4.14 (AB q, 2H), 4.02 (d, J=7.6 Hz, 1H), 2.49–1.08 (m, 23H, including singlets at 2.39, 2.14, 1.86, 1.20, 1.16, 3H each); HRMS calcd for C$_{55}$H$_{56}$NO$_{15}$ (MH): 970.3650, found: 970.3631.

EXAMPLE 3

7-Deoxy-8-desmethyl-7,8-cyclopropataxol (Ia)

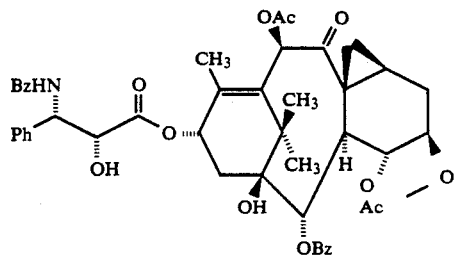

Compound IIIa (89 mg, 0.092 mmol) was dissolved in dry EtOAc (2 mL), and a catalytic amount of palladium on carbon (29.3 mg, 10%, 0.0276 mmol) was added. The reaction mixture was stirred under a hydrogen atmosphere for 5 h. The solvent was then evaporated and the residue was chromatographed on silica gel (eluted with 50% ethyl acetate in hexanes) to afford 74.3 mg (Y: 96.9%) of the title product; $^1$H-NMR (CDCl$_3$) δ 8.19–8.15 (m, 2H), 7.68–7.24 (m, 13H), 6.94 (d, J=9.0 Hz, 1H), 6.29 (s, 1H), 6.23 (m, 1H), 5.79 (dd, J=2.5 Hz, J'=8.9 Hz, 1H), 5.64 (d, J=7.7 Hz, 1H), 4.75 (dd, J=2.6 Hz, J'=4.9 Hz, 1H), 4.70 (m, 1H), 4.17 (AB q, 2H), 4.04 (d, J=7.6 Hz, 1H), 3.45 (d, J=4.9 Hz, 1H), 2.49–1.17 (m, 22H, including singlets at 2.39, 2.18, 1.79, 1.24, 1.20, 3H each); HRMS calcd for C$_{47}$H$_{49}$NO$_{13}$ (MH): 836.3249, found: 836.3249.

EXAMPLE 4

10-Deacetyl-bis-2',10-O-trichloroethyloxycarbonyl-taxol (IIb)

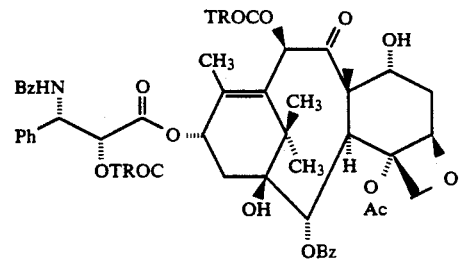

10-Deacetyl-7-epi-hydroxytaxol (186 mg, 0.229 mmol), prepared by the method of Kingston (J. Org. Chem. 1991, 56, 5114) Was dissolved in dry dichloromethane (4.6 mL). To this solution at 0° C. was added dry pyridine (74.2 μL, 0.917 mmol), followed by trichloroethyl chloroformate (94.7 μL, 0.688 mmol). The reaction was warmed to room temperature after 1 h, then stirred overnight. The solvent was then removed in vacuo, and the residue was purified by chromatography (eluted with 30–35% ethyl acetate in hexanes) to afford 206 mg (Y: 77.3%) of the title product as a foam; $^1$H-NMR (CDCl$_3$) δ 8.18–8.14 (m, 2H), 7.73–7.24 (m, 13H), 6.92 (d, J=9.6 Hz, 1H), 6.66 (s, 1H), 6.26 (m, 1H), 6.06 (dd, J=2.9 Hz, J'=9.5 Hz, 1H), 5.74 (d, J=7.4 Hz, 1H), 5.55 (d, J=2.9 Hz, 1H), 4.91 (dd, J=3.8 Hz, J'=8.6 Hz, 1H), 4.78 (m, 4H), 4.37 (AB q, 2H), 3.86 (d, J=7.4 Hz, 1H), 3.70 (m, 1H), 2.57–1.13 (m, 21H, including singlets at 2.56, 1.88, 1.67, 1.18, 1.13, 3H each); HRMS calcd for C$_{51}$H$_{52}$NO$_{17}$Cl$_6$ (MH): 160.1366, found: 1160.1322.

EXAMPLE 5

10-Deacetyl-bis-2',10-O-trichloroethyloxycarbonyl-8-desmethyl-7-deoxy-7,8-cyclopropataxol (IIIb) and compound XIb

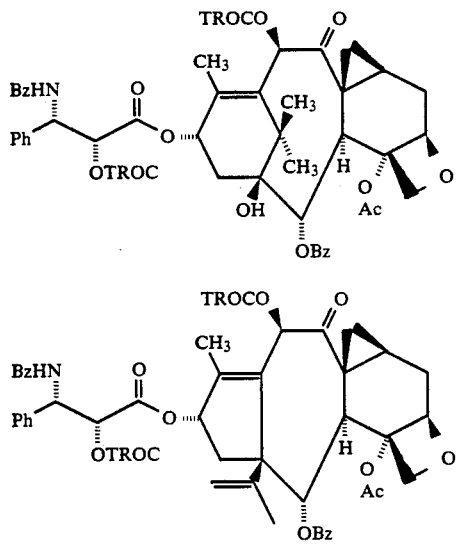

Compound IIb (124.6 mg, 0.107 mmol) was dissolved in dry dichloromethane (2.15 mL). To this solution at 0° C. was added DAST (28.3 μl, 0.214 mmol). After 2 h at that temperature, a second portion of DAST (14.2 μl, 0.107 mmol) was added. The reaction mixture was stirred at 0° C. for 1 h, then at room temperature for 16 h. The solvent was removed and the residue was chromatographed (eluted with 30–35% ethyl acetate in hexanes) to afford 56.5 mg (Y: 46.1%) of a mixture of cyclopropane derivatives IIIb and XIb together with 56.8 mg (45.6%) of remaining starting material IIb. The ratio of compound IIIb to XIb, as determined by HPLC, was 41/59. The two compounds were separated by HPLC (silica gel, eluted with 30% ethyl acetate in hexane).

Compound IIIb: $^1$H-NMR (CDCl$_3$) δ 8.19–8.16 (m, 2H), 7.70–7.32 (m, 13H), 6.91 (d, J=9.5 Hz, 1H), 6.27 (m, 1H), 6.11 (s, 1H), 6.06 (dd, J=2.7 Hz, J'=9.5 Hz, 1H), 5.66 (d, J=7.6 Hz, 1H), 5.52 (d, J=2.8 Hz, 1H), 4.72 (m, 1H), 4.78 (m, 4H), 4.18 (AB q, 2H), 4.03 (d, J=7.5 Hz, 1H), 2.48–1.21 (m, 20H, including singlets at 2.45, 1.91, 1.25, 1.21, 3H each); HRMS calcd for C$_{51}$H$_{50}$NO$_{16}$Cl$_6$(MH): 1142.1261, found: 1142.1228.

EXAMPLE 6

10-Deacetyl-7-deoxy-8-desmethyl-7,8-cyclopropataxol (Ib)

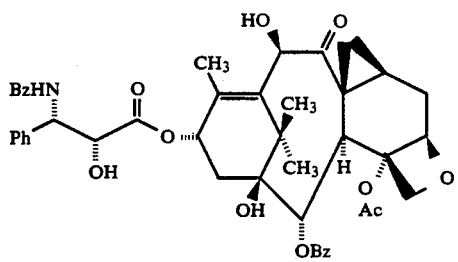

Compound IIIb (16.8 mg, 0.0147 mmol) was dissolved in acetic acid (0.4 mL) and methanol (0.6 mL). Zinc dust (28.1 mg, 0.44 mmol) was added. The reaction mixture was heated at 45° C. for 1.5 h. The solid was then filtered off. The filtrate was concentrated in vacuo, and the residue was chromatographed on silica gel (eluted with 60% ethyl acetate in hexanes) to afford 9 mg (Y: 77.6%) of the title product; $^1$H-NMR (CDCl$_3$) δ 8.18–8.15 (m, 2H), 7.69–7.24 (m, 13H), 6.99 (d, J=9.0 Hz, 1H), 6.25 (m, 1H), 5.80 (dd, J=2.2 Hz, J'=9.0 Hz, 1H), 5.64 (d, J=7.7 Hz, 1H), 4.97 (s, 1H), 4.75 (d, J=2.2 Hz, 1H), 4.70 (m, 1H), 4.20 (AB q, 2H), 4.21 (s, 1H), 4.07 (d, J=7.6 Hz, 1H), 2.40–1.16 (m, 20H, including singlets at 2.39, 1.79, 1.21, 1.16, 3H each); HRMS calcd for C$_{45}$H$_{47}$NO$_{12}$K (MH): 832.2735, found: 832.2741.

EXAMPLE 7

10-Deacetyloxy-10-oxo-7-epi-hydroxytaxol (Xa)

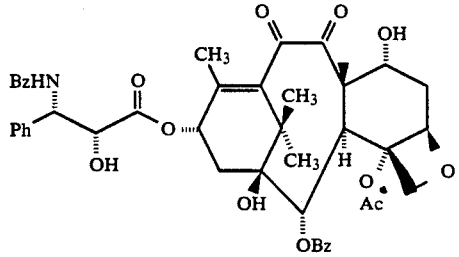

10-Deacetyl-7-epi-hydroxytaxol (162 mg, 0.200 mmol) was dissolved in dry dichloromethane (4 mL). To this solution at room temperature was added MnO$_2$ (521 mg, 6.00 mmoL). The reaction was stirred overnight at that temperature. The solvent was then removed, and the residue was chromatographed on silica gel (eluted with 60% ethyl acetate in hexanes) to afford 117 mg (Y: 72.2%) of the title compound; $^1$H-NMR (CDC$_3$) δ 8.19–8.12 (m, 2H), 7.72–7.25 (m, 13H), 6.97 (d, J=8.9 Hz, 1H), 6.21 (m, 1H), 5.86 (d, J=7.3 Hz, 1H), 5.78 (dd, J=2.4 Hz, J'=8.9 Hz, 1H), 4.89 (m, 1H), 4.80 (dd, J=2.5 Hz, J'=5.2 Hz, 1H), 4.44 (d, J=11.1 Hz, 1H), 4.38 (AB q, 2H), 4.01 (d, J=7.2 Hz, 1H), 3.85 (m, 1H), 3.61 (d, J=5.2 Hz, 1H), 2.52–1.10 (m, 20H, including singlets at 2.50, 2.03, 1.72, 1.22, 1.19, 3H each); HRMS calcd for C$_{45}$H$_{48}$NO$_{13}$ (MH): 810.3126, found: 810.3115.

EXAMPLE 8

2'-O-Allyloxycarbonyl-10-deacetyloxy-10-oxo-7-epihydroxytaxol (IIc)

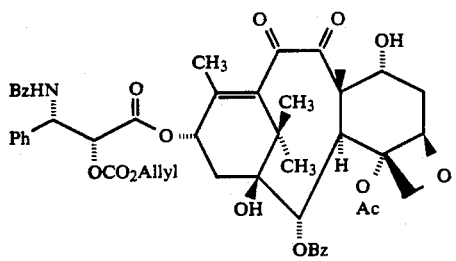

Compound Xa (136 mg, 0.140 mmol) was dissolved in dry dichloromethane (2.8 mL). To this solution at 0° C. was added dry pyridine (34.1 μL, 0.421 mmol), followed by allyl chloroformate (44.7 μL, 0.421 mmol). The reaction was stirred at room temperature overnight. The solvent was then removed in vacuo, and the residue was purified by silica gel chromatography (eluted with 40% ethyl acetate in hexanes) to afford 102.3 mg (Y: 81.6%) of the title product; $^1$H-NMR (CDCl$_3$) δ 8.17–8.13 (m, 2H), 7.72–7.33 (m, 13H), 6.94 (d, J=9.4 Hz, 1H), 6.20 (m, 1H), 5.98 (dd, J=2.6 Hz, J'=9.4 Hz, 1H), 5.91–5.82 (m, 2H), 5.43 (d, J=2.7 Hz, 1H), 5.36–5.24 (m, 2H), 4.89 (m, 1H), 4.63–4.32 (m, 5H), 4.00 (d, J=7.2 Hz, 1H), 3.82 (m, 1H), 2.53–1.08 (m, 20H, including singlets at 2.53, 1.88, 1.71, 1.17, 1.09, 3H each); HRMS calcd for C$_{49}$H$_{52}$NO$_{15}$ (MH): 894.3337, found: 894.335.

EXAMPLE 9

2'-O-Allyloxycarbonyl-10-deacetyloxy-10-oxo-8-desmethyl-7-deoxy-7,8-cyclopropataxol (IIIc) and compound XIc Compound IIc (102.3 mg, 0.114 mmol) was dissolved in dry dichloromethane (2.3 mL). To this solution at 0° C. was added DAST (30.3 μL, 0.229 mmol). After 2 h at that temperature, another dose of DAST (15.2 μL, 0.115 mmol) was added. The reaction was stirred at 0° C. for 1 h, and then left at room temperature overnight. The solvent was evaporated and the residue was chromatographed on silica gel (eluted with 30–35%

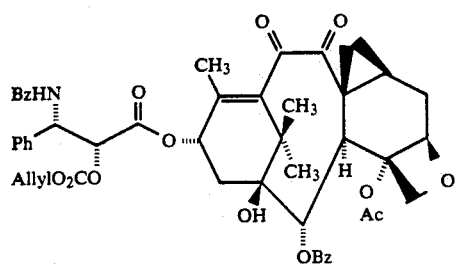

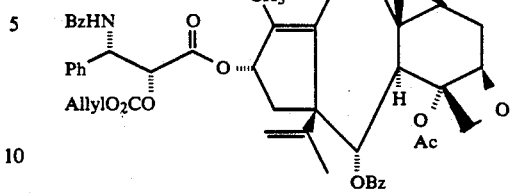

ethyl acetate in hexanes) to afford 40.5 mg (Y: 40.8%) of products IIIc and XIc together with 58 mg (Y: 56.7%) of starting compound IIc. The ratio of compound IIIc to XIc, as determined by HPLC, was 6:4. The compounds were separated by preparative HPLC (silica gel, eluted with 30% ethyl acetate in hexanes).

Compound IIIc: $^1$H-NMR (CDCl$_3$) δ 8.19–8.16 (m, 2H), 7.69–7.23 (m, 13H), 6.92 (d, J=9.4 Hz, 1H), 6.24 (m, 1H), 5.98 (dd, J=2.4 Hz, J'=9.5 Hz, 1H), 5.88 (m, 1H), 5.77 (d, J=7.6 Hz, 1H), 5.41 (d, J=2.4 Hz, 1H), 5.36–5.25 (m, 2H), 4.70 (m, 1H), 4.62 (m, 2H), 4.21 (AB q, 2H), 3.97 (d, J=7.4 Hz, 1H), 2.54–1.21 (m, 20H, including singlets at 2.43, 1.92, 1.30, 1.21, 3H each); HRMS calcd for C$_{49}$H$_{50}$NO$_{14}$ (MH): 876.3231, found: 876.3228.

EXAMPLE 10

10-Deacetyloxy-10-oxo-8-desmethyl-7-deoxy-7,8-cyclopropataxol (Ic)

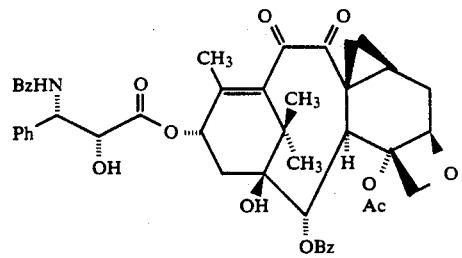

Compound IIIc (11.4 mg, 0.013 mmol) was dissolved in dry THF (0.5 mL), and the solution was degassed with dry N$_2$ for 2 min. A catalytic amount of Pd(PPh$_3$)$_4$ (0.30 mg, 0.00026 mmol) was added. To this solution at room temperature was added HOAc (3.7 μL, 0.065 mmol), followed immediately by Bu$_3$SnH (7.0 μL, 0.026 mmol). The reaction was complete in 40 min. The reaction mixture was diluted with CH$_3$CN (5 mL) and washed with hexanes (3×1 mL). The organic layer was concentrated in vacuo, and the residue was purified by silica gel chromatography (eluted with 60% ethyl acetate in hexanes) to afford 8.2 mg (Y: 79.6%) of compound Ic; $^1$H-NMR (CDCl$_3$): δ 8.21–8.15 (m, 2H), 7.71–7.31 (m, 13H), 6.90 (d, J=9.1 Hz, 1H), 6.23 (m, 1H), 5.81–5.74 (m, 2H), 4.77 (dd, J=2.5 Hz, J'=4.9 Hz, 1H), 4.69 (m, 1H), 4.20 (AB q, 2H), 3.98 (d, J=7.6 Hz, 1H), 3.47 (d, J=5.0 Hz, 1H), 2.52–1.14 (m, 20H, including singlets at 2.40, 1.84, 1.30, 1.22, 3H each); HRMS calcd for C$_{45}$H$_{46}$NO$_{12}$ (MH): 792.3020, found: 792.3037.

EXAMPLE 11

7-Triethylsilyloxy-10-deacetylbaccatin III (XXIX)

10-Deacetylbaccatin III (from Taxus baccata, 628.0 mg, 1.150 mmol) was dissolved in dry DMF (6 mL), cooled to 0° C., and treated with imidazole (312.8 mg, 4.595 mmol) and chlorotriethylsilane (0.772 mL, 4.60 mmol). The mixture was stirred at 0° C. for 4 h, then diluted with ethyl acetate (150 mL) and washed exhaustively with water and brine. The organic layer was dried and concentrated. The residue was purified by silica gel chromatography (being eluted with 50% ethyl acetate in hexane) to afford the title product as a foam (Y: 586 mg, 77%). This compound was described by Greene et al. in the *J. Am. Chem. Soc.*, 110, p 5917 (1988).

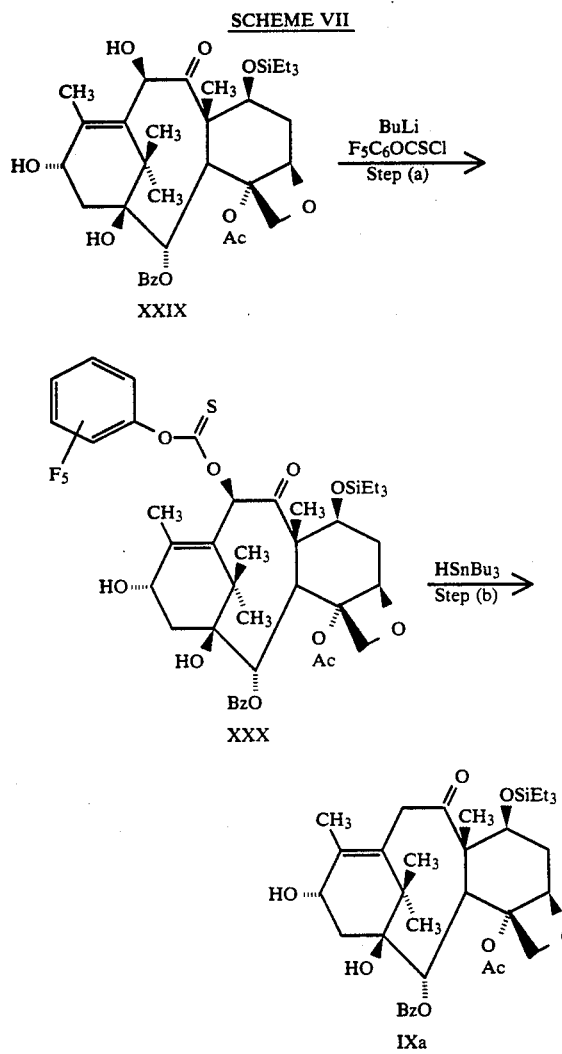

EXAMPLE 12

10-Pentafluorophenylthionocarbonate-7-triethylsilyloxybacoatin III (XXX)

Compound XXIX (319 mg, 0.485 mmol) was dissolved in dry THF (5 mL), cooled to −40° C., and treated with n-butyllithium (1.58M in hexanes, 0.384 mL, 0.606 mmol). After 40 min at this temperature, pentafluorophenyl chlorothionoformate (0.086 mL, 0.536 mmol) was added neat by a syringe. The reaction mixture was stirred at −20° C. for 90 min, then quenched with saturated ammonium chloride solution, and extracted with ethyl acetate. The ethyl acetate layer was dried and concentrated. The residue was purified by silica gel chromatography (being eluted with 40% ethyl acetate in hexane) to afford compound XXX as a foam (Y: 320 mg, 74%); $^1$H-NMR (CDCl$_3$) δ 8.09 (d, 2H) 7.56 (t, 1H) 7.44 (m, 2H) 6.78 (s, 1H) 5.64 (d, J=6.9 Hz, 1H) 4.96–4.89 (m, 2H) 4.49 (dd, J=10.2 Hz, J'=6.6 Hz, 1H) 4.12 (AB q, 2H) 3.80 (d, J=6.9 Hz, 1H) 2.55–0.44 (m, 43H); MS: 884 (MH+).

EXAMPLE 13

10-Deacetyloxy-7-triethylsilyloxybacctain III (IXa)

Thionocarbonate XXX (119 mg, 0.135 mmol) was dissolved in dry toluene (3 mL) and treated with AIBN (2 mg). The solution was degassed with dry nitrogen, then tributyltin hydride (0.055 mL, 0.202 mmol) was added. Subsequently, the solution was heated at 90° C. for 1 h. The solvent was evaporated and silica gel chromatography of the residue (being eluted with 40% ethyl acetate in hexane) gave compound IXa (Y: 87 mg, 99%) as a colorless foam; $^1$H-NMR (CDCl$_3$) δ 8.07 (d, J=8.2 Hz, 2H) 7.56 (bt, 1H) 7.44 (m, 2H) 5.57 (d, J=6.7 Hz, 1H) 4.92 (d, J=9.3 Hz, 1H) 4.78 (bs, 1H) 4.48 (dd, J=10.4 Hz, J'=6.6 Hz, 1H) 4.09 (AB q, 2H) 4.06 (d, J=6.7 Hz, 1H) 3.74 (d, J=14.8 Hz, 1H) 3.35 (bd, 1H) 2.44 (m, 1H) 2.25 (s, 3H) 2.22–0.45 (m, 42H); MS: 642 (MH+).

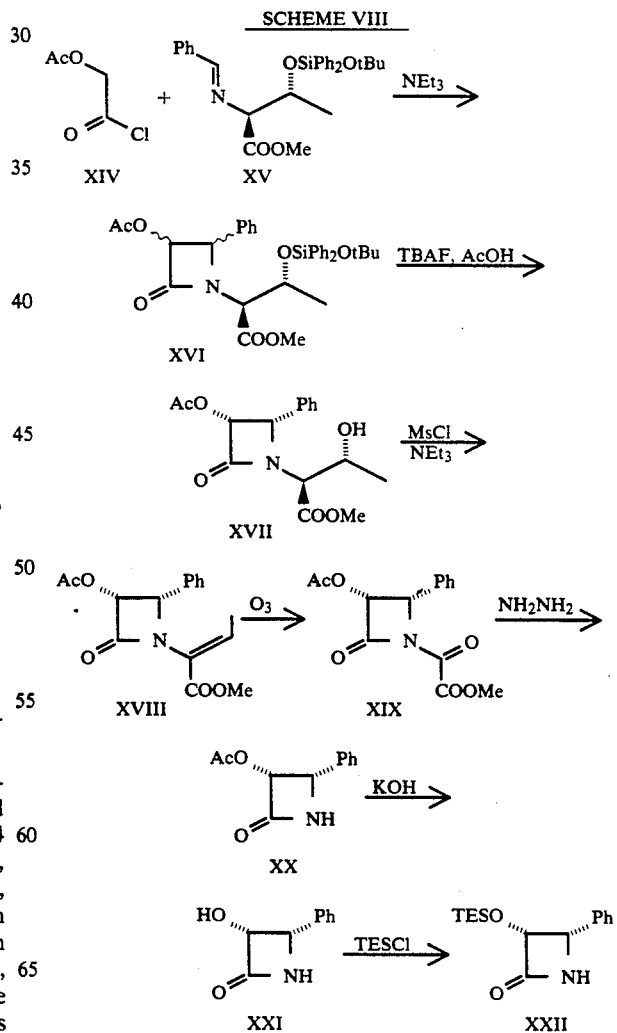

EXAMPLE 14

(3R, 4S)-4-Phenyl-3-triethylsilyloxy-2-azetidinone (XXII)

(L)-Threonine methyl ester hydrochloride (1.26 g, 7.44 mmol) in anhydrous dichloromethane (15 mL) was stirred with imidazole (1.01 g, 14.89 mmol) and t-butoxydiphenylsilyl chloride (2.274 g, 7.816 mmol) for 16 h at room temperature. The reaction mixture was partitioned between water and dichloromethane. The organic phase was washed with 5% aqueous sodium bicarbonate and water, dried and concentrated to give 2.88 g of a crude oil, which was used directly in the next step; $^1$H-NMR (CDCl$_3$) δ 7.70–7.25 (m, 10H) 4.44 (m, 1H) 3.62 (s, 3H) 3.31 (d, J=3 Hz, 1H) 2.12 (bs, 2H) 1.3–1.15 (m, 12H).

The foregoing oil (548 mg, 1.414 mmol) in anhydrous dichloromethane (10 mL) was treated with benzaldehyde (0.158 mL, 1.55 mmol) at room temperature overnight in the presence of 4 Å molecular sieves to afford compound of formula XV in situ. Upon cooling the solution containing compound XV to −40° C., triethylamine (0.20 mL, 1.698 mmol) was added, followed by acetoxyacetyl chloride (XIV) (0.182 mL, 1.698 mmol) over 10 min. The mixture was allowed to reach room temperature over 4 h and the product was partitioned between dichloromethane and water. The organic phase was further washed with water and brine, dried and concentrated. Silica gel chromatography (being eluted with 1:4 EtOAc/hexane) gave 411 mg of compound XVI as a ca. 10:1 mixture of 3R,4S : 3S,4R diastereomers.

This mixture of diastereomers (245.1 mg, 0.414 mmol) in dry THF (2 mL) was treated with acetic acid (0.15 mL) and tetrabutylammonium fluoride (TBAF, 1M in THF, 1.20 mL). The solution was stirred for 14 h at room temperature, then partitioned between ethyl acetate and 5% aqueous sodium bicarbonate. The organic phase was dried and concentrated. Flash silica gel chromatography using 1:1 ethyl acetate/hexane as eluent gave 66 mg (Y: 50%) of compound XVII (one diastereomer) as a foam; $^1$H-NMR (CDCl$_3$) δ 7.42–7.25 (m, 5H) 5.90 (d, J=4.8 Hz, 1H) 5.09 (d, J=4.8 Hz, 1H) 4.28 (m, 1H) 4.01 (d, J=4.8 Hz, 1H) 3.70 (s, 3H) 1.73 (s, 3H) 1.19 (d, J=6.6 Hz, 3H).

Compound of formula XVII (9.8 g, 0.0305 mol) in dry dichloromethane (100 mL) was treated at −78° C. with triethylamine (9.40 mL, 0.0671 mol) and methanesulfonyl chloride (MsCl, 3.50 mL, 0.0457 mol). The solution was allowed to reach room temperature overnight. The reaction mixture was partitioned between water and dichloromethane. The organic layer was washed with 5% aqueous sodium bicarbonate, dilute aqueous HCl, water and brine, and concentrated to afford compound XVIII as a crude oily residue. The crude residue (10.0 g) was dissolved in dichloromethane (250 mL) and ozone was passed through the solution at −78° C. until the solution retained blue color. Addition of methyl sulfide (11 mL) and concentration of the reaction mixture gave compound of formula XIX (crude).

Compound of formula XIX was dissolved in THF (150 mL) and treated at −78° C. with hydrazine hydrate (10 mL). After 2 h, the mixture was poured into dilute aqueous HCl and ethyl acetate, and the two phases were separated. The organic phase was washed with more acid, water and brine and concentrated to afford a crude product, which was purified by silica gel chromatography using 1–5% methanol in methylene chloride as eluent to yield 4.40 g (Y: 71%) of compound of formula XX; $^1$H-NMR (CDCl$_3$) δ 7.38–7.24 (m, 5H) 6.31 (bs, 1H) 5.87 (bm, 1H) 5.04 (d, J=4.8 Hz, 1H) 1.67 (s, 3H).

To a cooled (−5° C.) mixture of 1M aqueous KOH (140 mL) and acetonitrile (100 mL), a solution of compound XX (2.39 g, 11.22 mmol) in acetonitrile (130 mL) was added dropwise. The mixture was stirred at 0° C. for 1 h and diluted with ethyl acetate (300 mL), water (50 mL) and saturated aqueous bicarbonate (50 mL). The organic phase was separated, and the aqueous layer further extracted with ethyl acetate (3×200 mL). The organic phases were combined, dried, filtered and concentrated to give compound of formula XXI (crude), which was recrystallized from hexane/acetone (mp, 184°–6° C.); yield, 1.53 g (Y: 82%).

To azetidinone XXI (580 mg, 3.55 mmol) in dry THF (5.0 mL) was added imidazole (265.5 mg, 3.90 mmol), followed by triethylsilyl chloride (TESCl, 0.654 mL, 3.90 mmol). The mixture was allowed to be stirred for 1 h. Ethyl acetate was added and the organic layer was washed with brine, 10% aqueous HCl and dried. Silica gel chromatography (being eluted with 25% ethyl acetate in hexane) gave 670 mg (Y: 68%) of compound XXII as a foam.

EXAMPLE 15

(3R, 4S)-1-t-Butoxycarbonyl-4-phenyl-3-triethylsilyloxy-2-azetidinone (VIIIa)

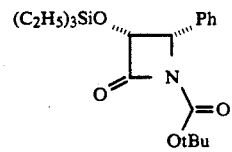

To a stirred solution of (3R, 4S)-4-phenyl-3-triethylsilyloxy-2-azetidinone (XXII) (2.200 g, 7.92 mmol) in dry THF (25 mL) was added N,N-diisopropylethylamine (1.65 mL. 9.510 mmol, 1.2 equiv) at 0° C. under an argon atmosphere. The solution was stirred for 5 min followed by the addition of di-t-butyl carbonate (2.080 g, 9.510 mmol, 1.2 equiv) and 4-dimethylaminopyridine (193.6 mg, 1.581 mmol, 0.20 equiv). The reaction mixture was stirred at 0° C. for 60 min. The solution was diluted by adding ethyl acetate (25 mL). The resulting solution was washed with brine, 10% NaHCO$_3$, 10% HCl solution, dried (MgSO$_4$), and concentrated to give a crude compound (oil). The compound was further purified by silica gel flash chromatography (being eluted with 15% ethyl acetate in hexanes) to afford 2.4 g (Y: 83%) of the title β-lactam as a white solid; $^1$H-NMR (CDCl$_3$) δ 7.28 (m, 5H) 5.03 (m, 2H) 1.39 (s, 9H) 0.76 (t, J=7.6 Hz, 9H) 0.43 (m, 6H).

EXAMPLE 16

(3R, 4S)-1-Benzoyl-4-phenyl-3-triethylsilyloxy-2-azetidinone (VIIIb)

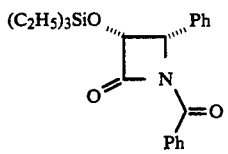

To a stirred solution of (3R, 4S)-4-phenyl-3-triethylsilyoxy-2-azetidinone (XXII) (1.000 g, 3.601 mmol) in dry $CH_2Cl_2$ (25 mL) was added N,N-diisopropylethylamine (0.689 mL, 3.961 mmol, 1.1 equiv) at 0° C. under an argon atmosphere. The solution was stirred for 5 min followed by the addition of benzoyl chloride (0.459 mL, 3.961 mmol, 1.1 equiv) and 4-dimethylaminopyridine (96.5 mg, 0.790 mmol, 0.20 equiv). The reaction mixture was stirred at room temperature for 1 h, then it was diluted with ethyl acetate (25 mL). The resulting solution was washed with brine, 10% $NaHCO_3$, 10% HCl solution, dried ($MgSO_4$), and concentrated to give a crude compound as an oil. The compound was further purified by silica gel flash chromatography (being eluted with 15% ethyl acetate in hexanes) which afforded 1.04 g (Y: 80%) of the title β-lactam as an oil; $^1$H-NMR (CDCl$_3$) δ 8.07–8.00 (m, 2H) 7.59–7.45 (m, 3H) 7.37–7.31 (m, 5H) 5.41 (d, J=6.1 Hz, 1H) 0.83–0.77 (m, 9H) 0.54–0.42 (m, 6H).

EXAMPLE 17

10-Deacetyloxytaxol (IVa)

10-Deacetyltaxol (XXIII) (140 mg, 0.173 mmol) in dry dichloromethane (3.5 mL) was treated at 0° C. with pyridine (0.028 mL, 0.346 mmol) and trichloroethyl chloroformate (0.0724 mL, 0.260 mmol). After 1 h at this temperature, the cold bath was removed and the mixture was stirred at room temperature overnight. The solvent was evaporated and the residue chromatographed on a silica gel column (being eluted with 30–50% ethyl acetate in hexane) to afford 92.3 mg (Y: 46%) of compound XXIV as a foam. Continued elution also afforded compound XXV in 16% yield as a foam.

Compound XXIV (92.3 mg, 0.079 mmol) in dry dichloromethane (2 mL) was treated with 1,1,2-trifluoro-2-chlorotriethylamine (0.0384 mL, 0.238 mmol). The solution was stirred overnight, the solvent evaporated, and the residue purified by silica gel chromatography (being eluted with 25% ethyl acetate in hexane) to yield 42.8 mg (Y: 47%) of compound XXVI as a white solid.

Dienone XXVI (39 mg, 0.034 mmol) was dissolved in methanol (0.5 mL) and acetic acid (0.5 mL). Zinc dust (66.4 mg, 1.02 mmol) was added, and temperature of the mixture was maintained at 40° C. for 1 h. The insoluble matter was removed by filtration. The filtrate was concentrated and silica gel chromatography of the residue (being eluted with 60% ethyl acetate in hexane) gave 22 mg (Y: 81.5%) of compound XXVII as a foam.

Dienone XXVII (22 mg, 0.028 mmol) in ethyl acetate (0.7 mL) was hydrogenated at slightly over one atmospheric pressure of hydrogen in the presence of 10% palladium on charcoal (14.7 mg) for 5.5 h at room temperature. Removal of the catalyst by filtration, and purification of the product by silica gel chromatography (being eluted with 1:1 ethyl acetate/hexane) gave 15 mg (Y: 68%) of compound IVa as a foam.

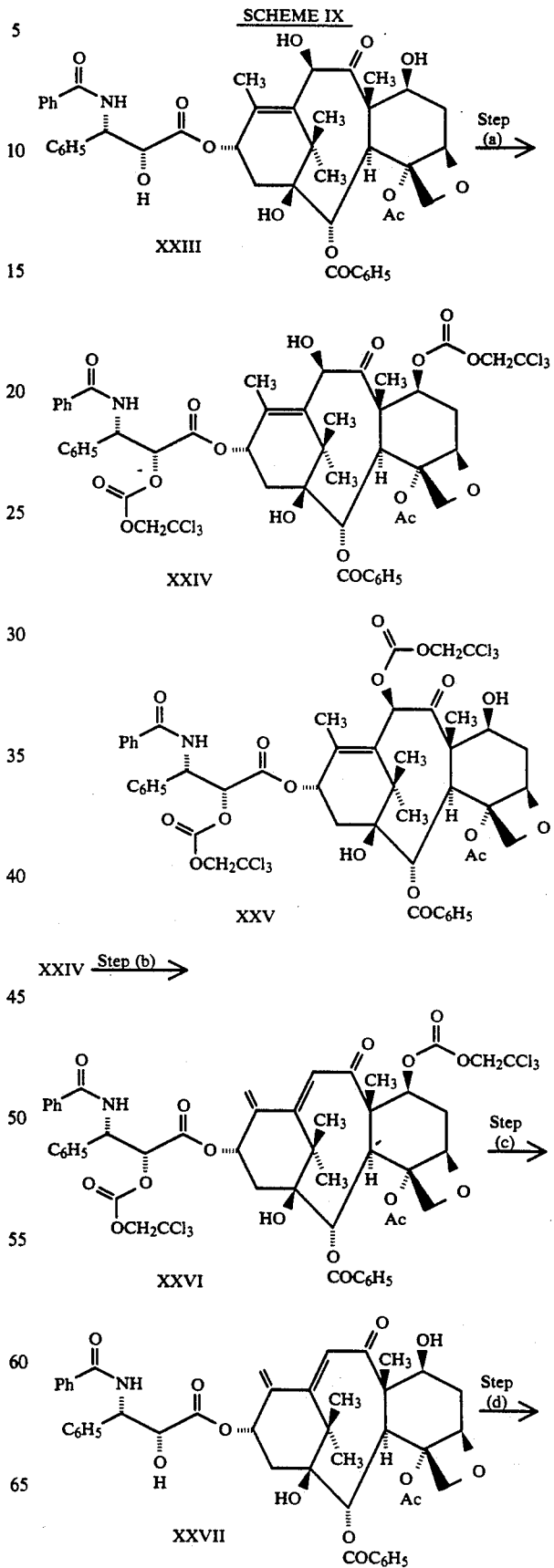

SCHEME IX

-continued
SCHEME IX

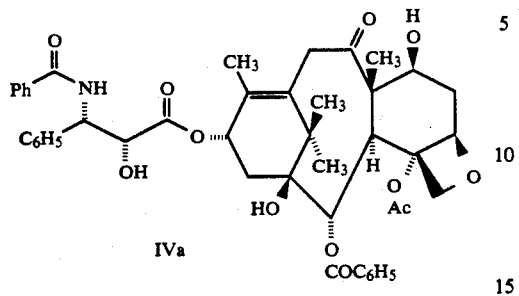

IVa

EXAMPLE 18

N-Debenzoyl-N-t-butyoxycarbonyl-10-deacetyloxytaxol (IVb)

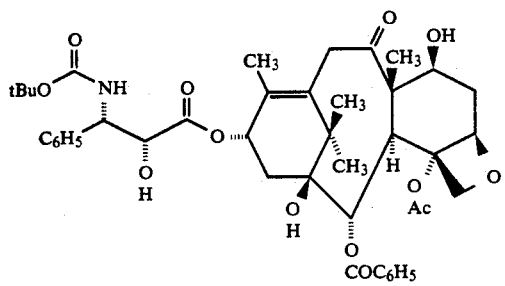

Compound IXa (100 mg, 0.156 mmol) was placed in a flask under argon and dissolved in dry THF (1.5 mL). Upon cooling to −40° C., n-butyllithium (1.45M in hexanes, 0.119 mL, 0.170 mmol) was added dropwise, followed by (3R,4S)-1-tert-butoxycarbonyl-4-phenyl-3-triethylsilyloxy-2-azetidinone (VIIIa) (94.2 mg, 0.25 mmol) in THF (0.5 mL) over a period of 2 min. The mixture was immediately warmed to 0° C. and stirred for 45 min before being quenched with saturated ammonium chloride (3 mL). The mixture was extracted with ethyl acetate, dried, and concentrated. Silica gel chromatography (eluted with 30% ethyl acetate in hexane) afforded N-debenzoyl-N-t-butoxycarbonyl-10-deacetyloxy-2',7-bis-O-(triethylsilyl)taxol as a foam (Y: 125 mg, 76%). This compound (100mg, 0.098 mmol) was immediately dissolved in acetonitrile (2 mL) at −5° C. and treated with hydrochloric acid (0.037 mL, 36%, 12M). The mixture was stirred for 2h at −5° C., then it was quenched with aqueous bicarbonate, extracted with ethyl acetate, and dried. Evaporation of the solvent was followed by silica gel chromatography (eluted with 75% ethyl acetate in hexane) to afford the title compound as a foam (Y: 80.5mg, 80%); $^1$H-NMR(CDCl$_3$) δ 8.10 (d, J=8.2 Hz, 2H) 7.64-7.29 (m, 8H) 6.11 (bt, 1H) 5.68 (d, J=6.9 Hz, 1H) 5.43 (bd, 1H) 5.25 (bd, 1H) 4.93 (d, J=7.7 Hz, 1H) 4.60 (bs, 1H) 4.30-4.18 (m, 3H) 4.02 (d, J=7.7 Hz, 1H) 3.80 (d, J=15.8 Hz, 1H) 3.46-3.40 (m, 2H) 2.62 (m, 1H) 2.35 (s, 3H) 2.35-2.25 (m, 2H) 1.89-1.65 (m, 5H) 1.63 (s, 3H) 1.35 (s, 9H) 1.19 (s, 3H) 1.16 (s, 3H).

EXAMPLE 19

2'-O-(Benzyloxycarbonyl)taxol (XXXIa)

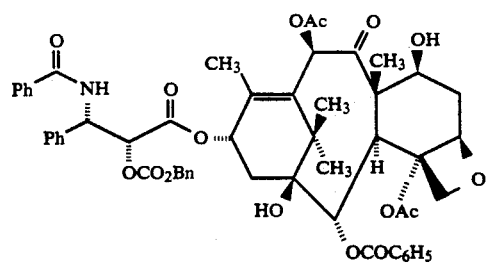

To a stirred solution of taxol (150 mg, 0.176 mmol) and N,N-diisopropylethylamine (93 μL, 0.534 mmol, 3 eq.) in anhydrous CH$_2$Cl$_2$ (4 mL) at room temperature was added benzyl chloroformate (75 μL, 0.525 mmol, 3 eq.) at room temperature. The reaction mixture was stirred at room temperature for 3 h. The reaction mixture was concentrated to 2 mL in volume and the product was purified on a silica gel column, using 1:1 of EtOAc/hexanes as eluant, to obtain 150 mg (0.152 mmol, Y:86%) of the title compound, XXXIa, as a white powder: mp, 140°–150° C. (decomposition); $[\alpha]_D^{20}$ −53.5° (c =0.2, 95% EtOH); $^1$H-NMR (300 MHz, acetone-d$_6$) δ ppm: 1.18 (3H, s, 17-H$_3$), 1.92 (3H, s, 16-H$_3$), 1.66 (3H, s, 19-H$_3$), 1.96 (3H, s, 18-H$_3$), 2.16 (3H, s, 10-OAc), 2.5 (3H, s, 4-OAc), 3.53 (1H, d, J=5.89 Hz, 7-OH, exchanged with D$_2$O), 3.85 (1H, d, J=7.19 Hz, 3-H), 3.9 (1H, s, 1-OH, exchanged with D$_2$O), 4.17 (2H, ABq, 20-H$_2$), 4.25 (1H, m, 7-H), 4.97 (1H, d, J=9.56 Hz, 5-H), 5.19 (2H, ABq, OCH$_2$C$_6$H$_5$), 5.54 (1H, d, J=5.5 Hz, 2'-H), 5.68 (1H, d, J=7.13 Hz, 2-H), 6.01 (1H, dd, J=5.5, 9.05 Hz, 3'-H), 6.17 (1H, bt, J=9.0 Hz, 13-H), 6.42 (1H, s, 10-H), 7.28-7.69 (16H, m), 7.87 (2H, "d", J=8 Hz, 3'-NHCOPh), 8.14 (2H, "d", J=8 Hz, 2-CO$_2$Ph), 8.55 (1H, d, J=9.06 Hz, NH, exchanged with D$_2$O); MS (FAB-NOBA/NaI+KI): m/e 988 (M+H)$^+$, 1010 (M+Na)$^+$, 1026 (M+K)$^+$; IR (KBr) ν max: 3448, 1748 (C=O), 1726 (CONH), 1250 (C-O) cm$^{-1}$; UV (MeOH:H$_2$O, 1:1) λ max: 198 (ε7.3×10$^4$), 230 nm (ε2.7×10$^4$).

HRMS calcd for C$_{55}$H$_{58}$NO$_{16}$ (MH+): 988.3756. Found: 988.3766.

Anal. calcd for C$_{55}$H$_{57}$NO$_{16}$.H$_2$O: C, 65.67; H, 5.92; N, 1.40. Found: C, 65.99; H, 5.64; N, 1.33.

EXAMPLE 20

2'-O-Benzyloxycarbonyl-7-deoxy-8-desmethyl-7,8-cyclopropataxol (IIIa)

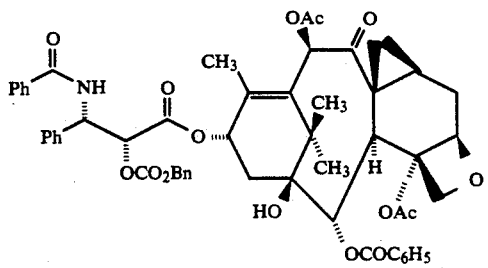

DAST (18.7 μL, 0.141 mmol) was dissolved in dry dichloromethane (0.5 mL), and this solution was cooled to 0° C. A solution of compound XXXIa (71 mg, 0.072 mmol) in dichloromethane (1 mL) was added and the resulting solution was kept at 0° C. for 30 min and at room temperature for 4 h. The water (0.15 mL) was added to the reaction mixture in order to quench the reaction and the resultant mixture was concentrated to leave a residue. The residue was chromatographed on a silica gel column (eluted with 40% ethyl acetate in hexane) to yield 61 mg (Y: 85.7%) of a 1:1 mixture compound IIIa and 2'-O-benzyloxycarbonyl-7-α-fluorotaxol as a white amorphous solid.

EXAMPLE 21

7-Dexoy-8-desmethyl-7,8-cyclopropataxol (Ia)

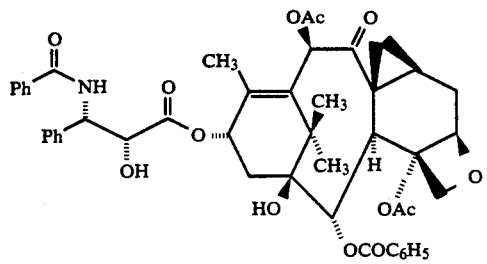

A 1:1 mixture of compound IIIa and 2'-O-benzyloxycarbonyl-7-α-fluorotaxol (89 mg) was dissolved in ethyl acetate (3 mL) and the mixture was stirred under slightly over one atmospheric pressure of hydrogen in the presence of palladium on charcoal (10% Pd, 29 mg, 0.027 mmol). After 12 h, the solvent was removed, and the residue was purified by silica gel chromatography (being eluted with 40% ethyl acetate in hexane) to afford 67.7 mg (Y: 88%) of the title compound, along with 7-α-fluorotaxol, as a white solid.

The following HPLC methods can be used to separate 7-α-fluorotaxol from compound Ia:

Method 1

Equipment

Pump: PE Series 4
Column: Shandon Hypercarb (graphitized carbon), 7 μ, 100×4.6 mm, #59864750 (information on preparative size columns may be obtained from Keystone Scientific, Bellefonte, Pa.)
Injector: PE ISS-100
Detector: HP-1040M

Conditions

Mobile Phase: 85:15 methylene chloride: hexane Separation not lost at 80:19:1 methylene chloride: hexane: isopropyl alcohol
Flow Rate: 2.5 mL/min
Detector: 254 nm
Diluent: Sample dissolved in methylene chloride

Method 2

Using DYNAMAX-60A (Si 83.121-C) preparative HPLC column (30cm×2.5cm) with 1:1 of ethyl acetate and hexane as eluant and the flow rate of 10 mL per min, the retention time for 7-α-fluorotaxol was 15.59 min, while the retention time for compound Ia was 16.65 min.

EXAMPLE 22

N-debenzoyl-N-t-butoxycarbonyl-2'-O-triethylsilyl-7-deoxy-8-desmethyl-7,8-cyclopropataxol (XXXVIIa)

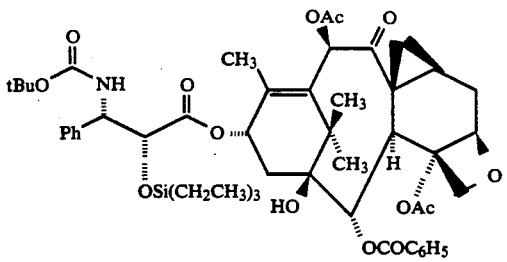

A mixture of compound Ia and 7-α-fluorotaxol (572 mg, 3:2 mixture) was treated with tetrabutylammonium borohydride (286 mg, 1.111 mmol) in dry dichloromethane (7 mL) at room temperature overnight. The excess borohydride was quenched with acetic acid (0.4 mL); the solvent was evaporated to leave a crude product. The crude product thus obtained was purified on a silica gel column (eluted with 50% ethyl acetate in hexane) to afford 271 mg (Y: 69%) of a mixture of 7-deoxy-8-desmethyl-7,8-cyclopropabaccatin III (XXXVa) and 7-α-fluoro baccatin III (XXXIVa) as a white foam.

A solution of compounds XXXVa and XXXIVa (130 mg) in dry THF (1 mL) was cooled to −40° C. and n-butyllithium (1.63M in hexane, 0.164 mL, 0.260 mmol) was added dropwise under argon. After 15 min, a solution of 1-t-butoxycarbonyl-(3R,4S)-cis-3-triethylsilyoxy-4-phenylazetidinone (VIIIa) (203 mg, 0.530 mmol) in dry THF (0.5 mL) was added, and the mixture was warmed to 0° C. The reaction was allowed to continue for 90 min at 0° C. and quenched with saturated aqueous ammonium chloride. The reaction mixture was extracted with ethyl acetate. The ethyl acetate layer was dried, filtered and concentrated in vacuo to leave a crude oil. This oil was purified by silica gel chromatography (eluted with 40% ethyl acetate in hexane) to provide 143 mg of the title compound, along with N-debenzoyl-N-butoxycarbonyl-2'-O-triethylsilyl-7-α-fluorotaxol (XXXVIa), as a white foam.

EXAMPLE 23

N-debenzoyl-N-t-butoxycarbonyl-7-deoxy-8-desmethyl-7,8-cyclopropataxol (Id)

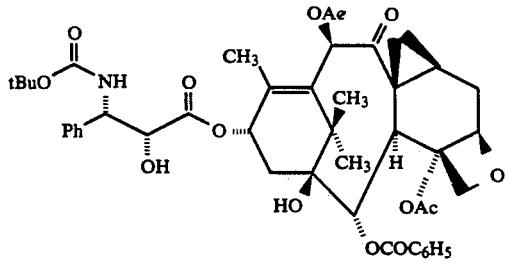

To a solution of a mixture of compounds XXXVIa and XXXVIIa (100 mg) in acetonitrile (1 mL) at −5° C. was added aqueous HCl (0.0192 mL, 0.30 mmol, 36% solution). The reaction mixture was stirred for 10 min and was diluted with ethyl acetate (1.5 mL). The organic phase was washed with water, dried, filtered, and concentrated to leave a residue. The residue was purified by silica gel chromatography (eluted with 40% ethyl acetate in hexane) to afford 73 mg of the title product, along with N-debenzoyl-N-t-butoxycarbonyl-7-α-fluorotaxol, as a foam.

EXAMPLE 24

Biological Study

The 7,8-cyclopropataxanes of the present invention showed in vitro cytotoxicity activity against human colon carcinoma cells HCT-116 and HCT-116/VM46. The HCT-116/VM46 cells are cells that have been previously selected for teniposide resistance and express the multi-drug resistance phenotype, including resistance to taxol. Cytotoxicity was assessed in HCT-116 human colon carcinoma cells by XTT (2,3-bis(2-methoxy-4-nitro-5-sulfpphenyl)-5-[(phenylamino)carbonyl]2H-tetrazolium hydroxide) assay as reported in D. A. Scudiero, et al., Evaluation of soluble tetrazolium/formazan assay for cell growth and drug sensitivity in culture using human and other tumor cell lines, *Cancer Res.* 48:4827–4833, 1988. Cells were plated at 4000 cells/well in 96 well microtiter plates and 24 hours later drugs were added and serial diluted. The cells were incubated at 37° C. for 72 hours at which time the tetrazolium dye, XTT, was added. A dehydrogenase enzyme in live cells reduces the XTT to a form that absorbs light at 450 nm which can be quantitated spectrophotometrically. The greater the absorbance, the greater the number of live cells. The results are expressed as an $IC_{50}$, which is the drug concentration required to inhibit cell proliferation (i.e., absorbance at 450 nm) to 50% of that of untreated control cells. The $IC_{50}$ values for compounds evaluated in this assay are given in the table below.

In vitro cytotoxicity of 7,8-cyclopropataxanes

| Compound | $IC_{50}$ (μg/ml) HCT-116 | $IC_{50}$ (μg/ml) HCT-116/VM46 |
| --- | --- | --- |
| Taxol | 0.005 | 0.428 |
| Ia | 0.008 | 0.183 |
| Ib | 0.030 | 0.869 |
| Ic | 0.058 | 0.948 |

Mice ip M109 Model

Balb/c×DBA/2 F$_1$ hybrid mice were implanted intraperitoneally, as described by William Rose in Evaluation of Madison 109 Lung Carcinoma as a Model for Screening Antitumor Drugs, *Cancer Treatment Reports*, 65, No. 3–4 (1981), with 0.5 mL of a 2% (w/v) brei of M109 lung carcinoma.

Mice were treated with compound under study by receiving intraperitoneal injections of various doses on days 5 and 8 post-implant. Mice were followed daily for survival until approximately 75–90 days post-tumor implant. One group of mice per experiment remained untreated and served as the control group.

Median survival times of compound-treated (T) mice were compared to the median survival time of the control (C) mice. The ratio of the two values for each compound-treated group of mice was multiplied by 100 and expressed as a percentage (i.e. % T/C) in Table I for a representative compound.

TABLE I

| Compound | IP M109 data<br>% T/C (dose in mg/kg/injection; schedule) |
| --- | --- |
| Ia | 156% (80, d. 5 & 8) |

The compounds of the instant invention have tumor inhibiting activities in mammals. Thus, another aspect of the instant invention concerns with a method for inhibiting mammalian tumors sensitive to a compound of formula I.

The present invention also provides pharmaceutical formulations (compositions) containing a compound of formula I in combination with one or more pharmaceutically acceptable, inert or physiologically active, carriers, excipients, diluents or adjuvants. Examples of formulating taxol or its related derivatives (including a possible dosage) are described in numerous literatures, for example in U.S. Pat. Nos. 4,960,790 and 4,814,470, and such examples may be followed to formulate the compounds of this invention. For example, the new compounds are administrable in the form of tablets, pills, powder mixtures, capsules, injectables, solutions, suppositories, emulsions, dispersions, food premix, and in other suitable forms. The pharmaceutical preparation which contains the compound is conveniently admixed with a nontoxic pharmaceutical organic carrier or a nontoxic pharmaceutical inorganic carrier, usually about 0.01 mg up to 2500 mg, or higher per dosage unit, preferably 50–500 mg. Typical of pharmaceutically acceptable carriers are, for example, mannitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

The compounds of the invention can also be freeze dried and, if desired, combined with other pharmaceutically acceptable excipients to prepare formulations suitable for parenteral, injectable administration. For such administration, the formulation can be reconstituted in water (normal, saline), or a mixture of water and an organic solvent, such as propylene glycol, ethanol, and the like.

The compounds of the present invention can be used in substantially the same manner as taxol for treating mammalian tumors. The mode, dosage and schedule of administration of taxol in human cancer patients have been extensively studied. See, for example *Ann. Int. Med.*, 111, pp 273–279 (1989). For the compounds of this invention, the dose to be administered, whether a single dose, multiple dose, or a daily dose, will of course vary with the particular compound employed because of the varying potency of the compound, the chosen route of administration, the size of the recipient and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. The dosage to be administered will be generally in the range of 0.8 to 8 mg/kg of body weight or about 50–275 mg/m² of the patient. An oncologist skilled in the art of cancer treatment will be able to ascertain, without undue experimentation, appropriate protocols for effective administration of the compounds of this present invention such as by referring to the earlier studies of taxol and its derivatives.

What is claimed is:

1. A compound of formula I

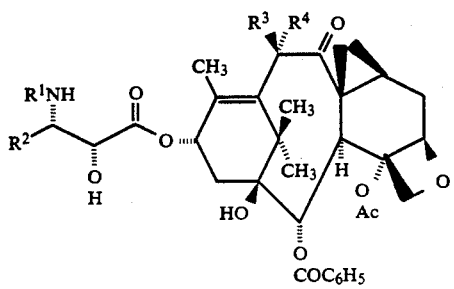

in which
- $R^1$ is —$COR^z$ in which $R^z$ is t-butyloxy, $C_{1-6}$ alkyl, $C_{2-6}$ alkenyl, $C_{2-6}$ alkynyl, $C_{3-6}$ cycloalkyl, or phenyl, optionally substituted with one to three same or different $C_{1-6}$ alkyl, $C_{1-6}$ alkoxy, halogen or —$CF_3$ groups;
- $R^2$ is $C_{1-6}$ alkyl, $C_{2-6}$ alkenyl, $C_{2-6}$ alkynyl, $C_{3-6}$ cycloalkyl, or a radical of the formula —W—$R^x$ in which W is a bond, $C_{2-6}$ alkenediyl, or —$(CH_2)_t$—, in which t is one to six; and $R^x$ is naphthyl, furyl, thienyl or phenyl, and furthermore $R^x$ can be optionally substituted with one to three same or different $C_{1-6}$ alkyl, $C_{1-6}$ alkoxy, halogen or —$CF_3$ groups;
- $R^3$ is OCOR, —OCOOR, H, or OH; $R^4$ is hydrogen; or $R^3$ and $R^4$ jointly form a carbonyl group; and R is $C_{1-6}$ alkyl.

2. A compound of claim 1 in which $R^1$ is benzoyl, and $R^2$ is phenyl.

3. The compound of claim 2 in which $R^3$ and $R^4$ taken together form a carbonyl group.

4. The compound of claim 2 in which $R^3$ is acetyloxy, and $R^4$ is hydrogen.

5. The compound of claim 2 in which $R^3$ is hydroxy, and $R^4$ is hydrogen.

6. The compound of claim 1 in which $R^1$ is t-butoxycarbonyl, and $R^2$ is phenyl.

7. The compound of claim 6 that is N-debenzoyl-N-t-butoxycarbonyl-7-deoxy-8-desmethyl-7,8-cyclopropataxol.

8. A pharmaceutical formulation which comprises as an active ingredient a compound as claimed in any one of claims 1 to 7 associated with one or more pharmaceutically acceptable carriers, excipients or diluents therefor.

9. A method for treating mammalian tumors which comprises administering to a mammal a tumor sensitive amount of a compound as claimed in any one of claims 1 to 7.

10. A compound of formula XXXV

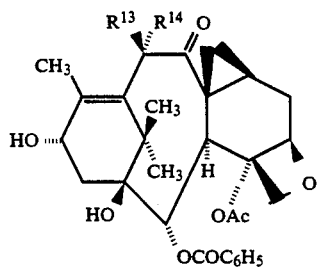

in which $R^{13}$ is hydrogen, acetyloxy or hydroxy; $R^{14}$ is hydrogen; or $R^{13}$ and $R^{14}$ jointly form a carbonyl group.

11. The compound of claim 10 in which $R^{13}$ is acetyloxy and $R^{14}$ is hydrogen.

* * * * *